US007592353B2

(12) United States Patent  
Ginn et al.

(10) Patent No.: US 7,592,353 B2
(45) Date of Patent: Sep. 22, 2009

(54) SUBSTITUTED 3-AMINO-THIENO[2,3-B]PYRIDINE-2-CARBOXYLIC ACID AMIDE COMPOUNDS AND PROCESSES FOR PREPARING AND THEIR USES

(75) Inventors: John David Ginn, New Milford, CT (US); Ronald John Sorcek, Bethel, CT (US); Michael Robert Turner, Danbury, CT (US); Erick Richard Roush Young, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 53 days.

(21) Appl. No.: 11/755,956

(22) Filed: May 31, 2007

(65) Prior Publication Data
US 2007/0293533 A1 Dec. 20, 2007

Related U.S. Application Data

(60) Provisional application No. 60/811,362, filed on Jun. 6, 2006.

(51) Int. Cl.
*A61K 31/4743* (2006.01)
*C07D 498/02* (2006.01)

(52) U.S. Cl. .............. 514/301; 514/233.8; 514/256; 514/274; 546/114

(58) Field of Classification Search ............ 514/301, 514/233.8, 256, 274
See application file for complete search history.

(56) References Cited

U.S. PATENT DOCUMENTS

| 5,350,748 | A | 9/1994 | Boschelli et al. |
| 5,656,638 | A | 8/1997 | Gaeta et al. |
| 5,852,046 | A | 12/1998 | Lang et al. |
| 6,232,320 | B1 | 5/2001 | Stewart et al. |
| 6,313,301 | B1 | 11/2001 | Miki et al. |
| 6,358,978 | B1 | 3/2002 | Ritzeler et al. |
| 6,579,882 | B2 | 6/2003 | Stewart et al. |
| 6,964,956 | B2 * | 11/2005 | Cywin et al. ........... 514/211.15 |
| 6,974,870 | B2 | 12/2005 | Cywin et al. |
| 7,119,102 | B2 | 10/2006 | Chen et al. |
| 7,291,733 | B2 | 11/2007 | Cywin et al. |
| 7,329,764 | B2 | 2/2008 | Chen et al. |
| 2001/0020030 | A1 | 9/2001 | Stewart et al. |
| 2005/0038104 | A1 | 2/2005 | Chen et al. |
| 2005/0282866 | A1 | 12/2005 | Ritzeler et al. |
| 2005/0288285 | A1 | 12/2005 | Cywin et al. |
| 2006/0019976 | A1 | 1/2006 | Karp et al. |
| 2006/0270671 | A1 | 11/2006 | Chen et al. |

FOREIGN PATENT DOCUMENTS

| CA | 2407593 A1 | 11/2001 |
| JP | 2005/194198 | 7/2005 |
| WO | WO 92/03427 | 3/1992 |
| WO | WO 95 /34548 | 12/1995 |
| WO | WO 00/61586 | 10/2000 |
| WO | WO 00/75145 A1 | 12/2000 |
| WO | WO 01/00610 A1 | 1/2001 |
| WO | WO 01/30774 A1 | 5/2001 |
| WO | WO 01/58890 A1 | 8/2001 |
| WO | WO 01/68648 A1 | 9/2001 |
| WO | WO 01/083456 A1 | 11/2001 |
| WO | WO 02/41843 | 5/2002 |
| WO | WO 02/051849 | 7/2002 |
| WO | WO 03/072561 A1 | 4/2003 |
| WO | WO 03/037886 A2 | 5/2003 |
| WO | WO 03/103661 A1 | 12/2003 |
| WO | WO 2006/030031 | 3/2006 |
| WO | WO 2006/043145 | 4/2006 |

OTHER PUBLICATIONS

ISR PCT/US2007/070053.
C. Nakanishi, et al., "Nuclear Factor-kB Inhibitors as Sensitizers to Anticancer Drugs". Nature Reviews, Cancer, vol. 5, Apr. 2005, pp. 297-309.
M.I. Abdel-Monem, et al., "Fluorine-containing heterocycles: synthesis and some reactions of new 3-amino-2-functionalized-6-(2'-thienyl)-4-trifluoromethylthieno[2,3-b]pyridines", Pharmazie, vol. 56, No. 1, p. 41, 2001.
F.A. Attaby, "Reactions of Styrylthienyl Ketone, Styryl Furyl Ketone with Thiocyanoacetamide: . . . ", Phosphorus, Sulfur, and Silicon. V139, n1 , pp. 1-12 1998.
P.A. Baeuerle, et al., "NF-kB: Ten Years After"; Cell, vol. 87, p. 13, 1996.
P.J. Barnes, "New Treatment for COPD", Nature Reviews Drug Discovery, vol. 1, p. 437, 2002.

(Continued)

*Primary Examiner*—Brian-Yong S Kwon
(74) *Attorney, Agent, or Firm*—Michael P. Morris; Mary-Ellen M. Devlin; Anthony P. Bottino

(57) ABSTRACT

Disclosed are compounds of formula (I):

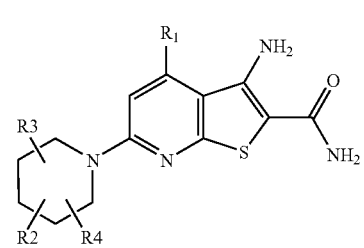

wherein $R_1$ and $R_4$ are defined herein, which are useful as inhibitors of the kinase activity of the IκB kinase (IKK) complex. The compounds are therefore useful in the treatment of IKK mediated diseases including autoimmune diseases inflammatory diseases, cardiovascular disease and cancer. Also disclosed are pharmaceutical compositions comprising these compounds and processes for preparing these compounds.

5 Claims, No Drawings

OTHER PUBLICATIONS

A.A. Beg, et al., "An Essential Role for NF-kB in Preventing TNF-alpha-Induced Cell Death", Science, vol. 274, p. 782, 1996.

J. Bondeson, et al., "Defining therapeutic targets by using adenovirus: Blocking NF-kB inhibits both inflammatory and destructive mechanisms in rheumatoid synovium but spares anti-inflammatory mediators", Proc. Natl. Acad. Sci. USA, vol. 96, p. 5668, 1999.

Y. Cao, et al., "IKKalpha Provides an Essential Link between RANK Signaling and Cyclin D1 Expression during Mammary Gland Development", Cell, vol. 107, p. 763, 2001.

O.T.M. Chan, et al., "The Central and Multiple roles of B Cells in Lupus Pathogenesis", Immunological Review, vol. 169, p. 107, 1999.

A. Distefano, et al., "Increased Expression of Nuclear Factor-kB in Bronchial Biopsies from Smokers and Patients with COPD", Eur. Respir. J., vol. 20, p. 556, 2002.

A. Gause, et al., "Role of B Cells in the Pathogenesis of Rheumatoid Arthritis", Biodrugs, vol. 15, No. 2, p. 73, 2001.

B. Haefner, "NF-kB: Arresting a Major Culprit in Cancer", Drug Discovery Today, vol. 7, No. 12. p. 653, 2002.

Y. Hu, et al., "Abnormal Morphogenesis but Intact IKK Activation in Mice Lacking the IKKalpha Subunit of IkB Kinase", Science, vol. 284, p. 316, 1999.

C. Jobin, et al., "Inhibition of Proinflammatory Molecule Production by Adenovirus-Mediated Expression of a Nuclear Factor kB Super-Repressor in Human Intestinal Epithelial Cells", J. Immunology, vol. 160, p. 410, 1998.

E.I. Kaigorodova, et al., "Synthesis of Substituted 2-Alkyl(Aryl)Thio-3-Cyanopyridines and 3-Aminothieno[2,3-b]Pyridines", Chemistry of Heterocyclic Compounds, vol. 32, No. 10, p. 1234, 1996.

M. Karin, et al., "NF-kB in Cancer: From Innocent Bystander to Major Culprit", Nature Reviews Cancer, vol. 2, p. 301, 2002.

M. Karin, et al., "the IkB Kinase (IKK) and NF-kB: key elements of Proinflammatory Signalling", Seminars in Immunology, vol. 12, p. 85, 2000.

A. Krauze, et al., "Derivatives of 3-cyano-6-phenyl-4-(3'-pyridyl)-pyridine-2(1H)-Thione and their Neurotropic Activity". Eur. J. Med. Chem, vol. 34, p. 301, 1999.

I. Lavon, et al., "High Susceptibility to Bacterial Infection, But no Liver Dysfunction, in Mice Compromised for Hepatocyte NF-kB activation", Nature Medicine, vol. 6, No. 5, p. 573, 2000.

Q. Li, et al., "Severe Liver Degenaration in Mice Lacking the IkB Kinase 2 Gene", Science, vol. 284, p. 321, 1999.

P. Libby, "Atherosclerosis: The New View", Scientific American, p. 46, 2002.

A. Pahl, et al., "Asthma Therapy in the New Millennium", Inflammation Research, vol. 51, p. 273, 2002.

V.J. Palombella, et al., "The Ubiquitin-Proteasome Pathway is Required for Processing the NF-kB1 Precursor Protein and the Activation of NF-kB", Cell, vol. 78, p. 773, 1994.

R. Seetharaman, et al., "Essential Role of T Cell NF-kB Activation in Collagen-Induced Arthitis", J. Immunology, vol. 163, p. 1577, 1999.

U. Senftleben, et al., "Activation by IKKalpha of a Second, Evolutionary Conserved, NF-kB Signaling Pathway", Science, vol. 293, p. 1495, 2001.

Y. Sharanin, et al., "Cyclizations of Nitriles. LVI.* Synthesis and Transformations of Substituted 6-Aryl-3-cyano-4-(2-thienyl)-pyridine-2(1H)-thiones", J. Org. Chem USSR. ENG TRNS, v32, No. 8, p. 1207, 1996 Translated from Zburnal Organicheskoi Khimii vol. 32, No. 8, 1996, pp. 1251.

A.M. Shestopalov, et al., "Synthesis Based on 2-Aryl-3-Aroyl-1,1-Dicyanopropanes", J. Org. Chem USSR Eng Trns, v20 p. 1382, 1984.

U. Siebenlist, et al., "Structure, Regulation, and Function of NF-kB", Ann. Rev. Cel.l Biol. vol. 10, p. 405, 1994.

A. O. Stewart, at al., "Discovery of Inhibitors of Cell Adhesion Molecule Expression in Human Endothelial Cells, 1. Selective Inhibition of ICAM-1 and E-Selectin Expression", J. Med. Chem., vol. 44, p. 988, 2001.

K. Takeda, et al., "Limb and Skin Abnormalities in Mice Lacking IKKalpha", Science, vol. 284, p. 313, 1999.

G. Wagner, Pharmazie "Synthese Neuer Prim., Sek. und tert. 3-Amino-Thieno [2,3-b]pyridin-2-car-Bon Saeureamide auf verschiedenen Wegen" 1990, vol. 45, No. 2 p. 102.

G. Wagner, et al., "Synthese neuer Pyrido[3',2':4,5]thieno[3,2-d]1,2,3-triazin-Derivate als Antianaphylaktika", Pharmazie, 1993, v48, p. 514.

M-J Yin, et al., "The Anti-Inflammatory agents aspirin and salicylate inhibit the activity of IkB Kinase-B", Nature, vol. 396, p. 77, 1998.

Case 9-281-1-D1, U.S. Appl. No. 11/836,590, filed Aug. 9, 2007; Substituted Tricyclic heterocycles and Their Uses.

Karin, et al. "The IKK NF-kB System: A Treasure Trove for Drug Development" Nature Reviews Drug Discovery, 2004, vol. 3, No. 1, p. 17.

Nakanishi, et al., Nature Reviews Cancer Apr. 2005, v5, p. 297.

Sausville, et al., "Contributions of human tumor xenografts to anti-cancer drug development" Cancer Research, 2006, vol. 66, p. 3351.

Johnson, et al., "Relationships between drug activity in NCI preclinical in vitro and in vivo models and early clinical trials." British J. ofCancer, 2001, vol. 84, No. 10, p. 1424.

Vitali, T., et al., "Proprieta Biologiche di Composti 1,2-benzisotiazolici" Ateneo Parmense Acta Naturalia, vol. 7, No. 1, 1971, p. 71-109, xp009040652.

S.W. Schneller, et al., "Fused Thieno[3,2-d]-v-Triazine-4(3H)-Ones", Heterocycles, vol. 3, No. 2, 1975, p. 135-138, xp009040651.

Beck, J.R., et al., "Synthesis of [1] Benzothieno [3,2-d]-v-triazine Derivatives. A unique Diazonium Ion Cyclization", J. Org. Chem., vol. 41, No. 10, 1976, pp. 1733-1734, XP002244950.

J. Markert, et al., "Neue Synthesen Mit Elementarem Schwefei Darstellung Von 1,2-Benzisothiazolen und Einige Folgereaktionen" (New Synthesis with Elemental Sulfur—Preparation of 1,2-Benzisothiazoles and Some secondary reactions) Liebigs Ann. Chem., vol. 5, 1980, p. 768-778, XP000567752.

Abdel-Hafez, A.A., et al., "New Benzothiophene Derivatives I. A Convenient Synthesis of Novel Benzothienotriazines"; Bull. Fac. Sci., Assiut. Univ., 22 (2-B), pp. 63-78 (1993).

T.S. Shah, et al., "Pharmacological Evaluation of LM-2616: A Beta 1-Adrenoceptor Antagonist with Beta2-Adrenoceptor Agonistic Activity", Pharm. Comm. 1995, vol. 5, pp. 253-265.

K.G. Dave, et al., "Reaction of Nitriles under acidic conditions, part 1. A General method of Synthesis of Condensed Pyrimidines", J. Heterocyclic Chem. vol. 17, 1980, pp. 1497-1500.

V.A. Artyomov, et al., "N-Cyanochloroacetamidine—a Convenient Reagent for the Regioselective Synthesis of Fused Diaminopyrimidines", Tetra. vol. 52, No. 3, pp. 1011-1026, 1996.

Kadushkin, et al., Khimiko-Farmatsevticheskii Zhurnal (1992_, v26, (11-12), p. 62-66 Abstract as cited by examiner.

A. S. Baldwin, Jr., "The NF-kB and IkB Proteins: New Discoveries and insights" Annual Review Immunology, 1996, vol. 14, p. 649-681.

Toshiki Murata, et al., Discovery of Novel and Selective IKK-B Serine- Threonine Protein Kinase Inhibitors, Part 1, Bioorganic & Medicinal Chem letters, 2003, vol. 13, p. 913-918, Elsevier Science Ltd.

XP-002254095 Abstract, "Synthesis of Novel heterocyclic Compounds for Antitumor and Radioprotective Activities".

M.M. Ghorab, et al., "Synthesis of Novel Heterocyclic Compounds for Antitumor and Radioprotective Activities", Phosphorus, Sulfur, and Silicon, 1998, vol. 134/135, pp. 447-462.

XP-002254099 Abstract, "Use of benzo- and pyrido-furan or—thiophane cpds.—as hypercalcaemia agents for treating osteoporosis".

XP-002254097 Abstract, "Synthesis and Antimicrobial Evaluation of Several new Pyridine, Thienopyridine and Pyridothienopyrazole Derivatives".

Attaby, et al., "Synthesis and Antimicrobial Evaluation of Several new Pyridine, Thienopyridine and Pyridothienopyrazole Derivatives" Phosphorus, Sulfur, and Silicon, 1999, vol. 149, p. 49-64.

ISR 9-386 PCT.

H. Saitoh, et al., "Effect of Antisense Oligonucleotides to Nuclear Factor-k-B on the Survival of LPS-induced ARDS in Mouse". Experimental Lung Research, 2002, vol. 28, pp. 219-231.

M. Holmes-McNary. "Nuclear factor kappa B signaling in catabolic disorders". Current Opinion Clinical Nutrition Metabolic Care, 2002, vol. 5, No. 3, pp. 255-263, Lippincott Williams & Wilkins.

Y. Han, et al., "TNF-a medicates SDF-1-a-induced NF-kB activation and cytotoxic effects in primry astrocyles". The Journal of Clinical Investigation, 2001, vol. 108, No. 3, pp. 425-435.

XP002254098—Chemical Abstract. Copyright 1988-2001 Beilstein Institut zur Foerderung deter Chemischen Wissenschaften.

XP001154945. G. Wagner, et al., "Synthesis of new primary, secondary, and tertiary 3-amino-thieno[2,3-b]pyridine-2-carboxamides by various pathways". Biosciences Section of the Karl Marx University Leipzig, Field of Chemistry of Biologically Active Compounds, Pharmazie 45, 1990, pp. 102-109.

G. Wagner, et al., "Synthesis of new pyrido (3',2',4,5) thieno (3,2-d) 1,2,3-triazine derivatives as antianaphyactics". Pharmazie (Pharmacy), 48, vol. 7, 1993, pp. 514-518.

* cited by examiner

SUBSTITUTED 3-AMINO-THIENO[2,3-*B*]PYRIDINE-2-CARBOXYLIC ACID AMIDE COMPOUNDS AND PROCESSES FOR PREPARING AND THEIR USES

RELATED APPLICATIONS

This application claims the benefit under 35 U.S.C. §119 (e) U.S. provisional application No. 60/811,362, filed Jun. 6, 2006 the contents of which are incorporated herein.

TECHNICAL FIELD OF THE INVENTION

This invention relates to substituted 3-amino-thieno[2,3-b] pyridine-2-carboxylic acid amide compounds useful as inhibitors of the kinase activity of the IκB kinase (IKK) complex. The compounds are therefore useful in the treatment of IKK-mediated diseases including autoimmune diseases, inflammatory diseases and cancer. The invention also relates to processes for preparing such compounds and pharmaceutical compositions comprising them.

BACKGROUND OF THE INVENTION

NF-κB or nuclear factor κB is a transcription factor that induces the expression of a large number of pro-inflammatory and anti-apoptotic genes. These include cytokines such as IL-1, IL-2, TNF-α and IL-6, chemokines including IL-8 and RANTES, as well as other pro-inflammatory molecules including COX-2 and cell adhesion molecules such as ICAM-1, VCAM-1, and E-selectin. The NF-κB family includes homo- and heterodimeric transcription factors composed of members of the Rel family (see for example P. A. Baeurle and D. Baltimore, *Cell,* 1996, 87, 13). Under resting conditions, NF-κB is present in the cytosol of cells as a complex with IκB. The IκB family of proteins serve as inhibitors of NF-κB, interfering with the function of its nuclear localization signal (see for example U. Siebenlist et al., *Ann. Rev. Cell Biol.,* 1994, 10, 405). Upon disruption of the IκB-NF-κB complex following cell activation, NF-κB translocates to the nucleus and activates gene transcription. Disruption of the IκB-NF-κB complex and subsequent activation of NF-κB is initiated by degradation of IκB.

Upon cellular activation by a variety of pro-inflammatory stimuli including IL-1, TNF-α and LPS (bacterial lipopolysaccharide), two specific serine residues of IκB are phosphorylated. Upon phosphorylation, IκB undergoes polyubiquination and subsequent degradation by the 26S proteasome (see for example V. J. Palombella et al., *Cell,* 1994, 78, 773), freeing NF-κB to translocate to the nucleus. The phosphorylation of IκB is carried out by the IκB kinases (see for example a review by M. Karin and M. Delhase, *Seminars in Immunology,* 2000, 12, 85). The traditional IKK complex includes at least three subunits, IKKα (also called IKK-1), IKKβ (or IKK-2) and IKKγ (or NEMO), although other relevant complexes involving IKKα and IKKβ may exist. IKKα and IKKβ are both catalytic subunits while IKKγ is believed to be a regulatory subunit. Both IKKα and IKKβ can phosphorylate IκB. For the purposes of this document, the terms IKK or IKK complex refers to any complex that has kinase activity derived from IKKα and/or IKKβ subunits.

In vivo, activation of IKK occurs upon phosphorylation of its catalytic subunit. Both IKKα and IKKβ can be phosphorylated on serine residues, S177 and S181 of the activation loop in the case of IKKβ, and S176 and S180 of the activation loop for IKKα. An IKKβ mutant having alanines in place of serines at 177 and 181 prevented IKKβ phosphorylation and subsequent activation of the IKK complex by TNFα, IL-1 and other upstream activators. These results support a key role for IKKβ in phosphorylation of IκB following proinflammatory stimulation.

Studies in which the NF-κB pathway has been inhibited in cells and animals support the concept that inhibition of the phosphorylation of IκB is a viable approach to treatment of inflammatory, autoimmune and other diseases. In these studies, NF-κB activation was prevented by expression of a non-degradable version of the IκB protein. Expression of this inhibitor in synovial cells derived from rheumatoid arthritis patients reduced the expression of TNF-α, IL-6, IL-1β and IL-8 while the anti-inflammatory molecules IL-10, IL-1ra and IL-11 were not affected. Matrix metalloproteinases (MMP1 and MMP3) were also down-regulated (J. Bonderson et al., *Proc. Natl. Acad. Sci. U.S.A.,* 1999, 96, 5668). Transgenic expression of the IκB inhibitor in T cells caused a significant reduction in the severity and onset of collagen-induced arthritis in mice (R. Seetharaman et al., *J. Immunol.* 1999, 163, 1577). These experiments indicate that suppression of NF-κB in the diseased joint could reduce both the severity and progression of RA. In primary intestinal epithelial cells, the NF-κB inhibitor blocked the expression of IL-1, IL-8, iNOS and COX-2, mediators that are up-regulated during the course of inflammatory bowel disease (C. Jubin et al., *J. Immunol.,* 1998, 160, 410). Expression of this inhibitor in certain tumor cells enhances killing of these cells by chemotherapeutic reagents (A. A. Beg and D. Baltimore, *Science,* 1996, 274, 782).

Analysis of biopsies from lungs of patients with chronic obstructive pulmonary disease (COPD) found an increased expression of NF-κB that correlated with disease severity (A. Di Stefano et al., *Eur. Resp. J.,* 2002, 1, 437). Inhibition of NF-κB activation with inhibitors of IKK-β was among the anti-inflammatory approaches reported to be potentially useful in the treatment of COPD (P. J. Barnes, *Nature Rev. Drug Disc.,* 2002, 1, 437). Likewise, inhibition of NF-κB activity has been mentioned as a therapeutic approach for asthma (A. Pahl and I. Szelenyi, *Infl. Res.,* 2002, 51, 273).

A recent review describes the essential role of inflammatory mediators in the development cardiovascular disease. The inflammatory mediators and the cells that they recruit are reported to play a key role in the development of fatty streaks and plaques that lead to atherosclerosis. In addition they are reported to play a key role in subsequent degradation of the fibrous cap that forms over the plaque, leading to rupture and clot formation. If the clot grows large enough it can lead to myocardial infarction or stroke. Thus, anti-inflammatory drugs that can inhibit the production of these mediators and subsequent recruitment and activation of these cells may be beneficial in treatment of these diseases (P. Libby, *Scientific American,* 2002, 46).

A number of studies indicate that activation of NF-κB also plays a key role in the pathogenesis and development of cancer (see for example reviews by B. Haefner, *Drug Disc. Today,* 2002, 7, 653 and M. Karin et al., *Nat. Rev.* Cancer, 2002, 2, 301). Studies have shown that cells in which NF-κB is constitutively active are resistant to apoptosis. This can contribute to carcinogenesis by preventing cell death in cells that have undergone chromosomal changes or damage. In addition tumor cells with constitutively active NF-κB are resistant to anti-cancer therapies including chemotherapy and radiation. Further studies have linked activated NF-κB to a variety of lymphoid-, myeloid- and epithelial-derived malignancies including leukemia, lymphomas and breast, gastric, colorectal, lung, and pancreatic cancers. Thus it is suggested that inhibitors of NF-κB, including inhibitors of IKKα and IKKβ, may be useful either alone or in combination with other anti-cancer therapies in treating cancer.

Collectively, the studies described above provide support that inhibition of NF-κB function through inhibition of IKK may be a useful therapeutic approach to treatment of autoimmune and inflammatory disease, cardiovascular disease and cancer.

Studies have also been done in mice with targeted disruption of the IKKβ gene. Knockout of the IKKβ gene resulted in embryonic lethality due to apoptosis of hepatocytes. However, fibroblasts from the IKKβ knockouts did not undergo IKK and NF-κB activation upon stimulation with IL-1 or TNFα (Q. Li et al., *Science*, 1999, 284, 321), supporting a key role for IKKβ in and NF-κB activation following inflammatory stimuli.

A conditional knockout was generated by expressing a liver-specific inducible dominant negative IκBα transgene (I. Lavon et al., *Nature Medicine*, 2000, 6, 573). These mice were viable with no signs of liver dysfunction even after one year but they did have impaired immune function. This study supports the idea that inhibition of IKKβ can result in immune suppression without damage to the liver.

IKKα knock-out mice died shortly after birth and displayed a variety of skeletal defects and skin abnormalities. Fibroblast and thymocytes from these mice showed normal IKK activation and IκB degradation in response to TNFα, IL-1 or LPS (Y. Hu et al., *Science*, 1999, 284, 316; K. Takeda et al., *Science*, 1999, 284, 313). Recent studies with knockout and knock-in mice have revealed distinct roles for IKKα in development and cell signaling. In contrast to the studies with IKKα knock-out mice, mice having a kinase inactive version of IKKα knocked in are viable and fertile, indicating that the perinatal lethality and abnormalities seen in the IKKα knock-out mice are not due to the lack of kinase activity. However, these mice do have defects in B cell maturation and development of secondary lymphoid organs (U. Senftleben et al., *Science*, 2001, 293, 1495). This phenotype appears to be due to a defect in processing of the NF-κB2/p100 protein to p52, the DNA binding form of this member of the Rel family of transcription factors. In turn, this leads to a defect in the activation of a subset of NF-κB target genes in B cells. In addition, other studies with these same mice have shown that IKKα kinase activity is required for NF-κB activation in the mammary epithelium during pregnancy (Cao, Y., et. al., *Cell*, 2001, 107, 763). This pathway is specifically activated through the TNF receptor family member RANK, requires phosphorylation of the canonical IKK substrate IκBα, and culminates in induction of the cell cycle regulatory gene Cyclin D1.

These studies indicate that an inhibitor of IKKα kinase activity may be useful in treating diseases associated with inappropriate B cell activation such as lupus (O. T. Chan et al., *Immunological Rev.*, 1999, 169, 107) and rheumatoid arthritis (A. Gause and C. Borek, *Biodrugs*, 2001, 15, 73). In addition, an inhibitor of IKKα may be useful in the treatment of breast cancer since NF-κB is constitutively active in a number of breast tumors and many of these tumors depend on Cyclin D1 for proliferation.

Inhibitors of IKKβ have been reported. WO 01/58890 and WO 03/037886 describes heteroaromatic carboxamide derivatives as inhibitors of IKKβ. WO 01/68648 describes substituted β-carbolines having IKKβ inhibiting activity. Substituted indoles having IKKβ inhibitory activity are reported in WO 01/30774. WO 01/00610 describes substituted benzimidazoles having NF-κB inhibitory activity. Aspirin and salicylate have been reported to bind to and inhibit IKKβ (M. Yin et al., *Nature*, 1998, 396, 77).

Substituted thienopyridines having cell adhesion inhibiting activity are reported in US 2001/0020030 A1 and A. O. Stewart et al., *J. Med. Chem.*, 2001, 44, 988. Thienopyridines exhibiting gonadotropin releasing hormone antagonizing activity are reported in U.S. Pat. No. 6,313,301. Substituted thienopyridines described as telomerase inhibitors are disclosed in U.S. Pat. No. 5,656,638.

A number of 4,6-disubstituted thieno[2,3-b]pyridine-2-carboxylic acid amides have been described in the chemical literature. Examples include 3-amino-4,6-dimethyl-thieno[2,3-b]pyridine-2-carboxylic acid amide, 3-amino-6-methyl-thieno[2,3-b]pyridine-2,4-dicarboxylic acid diamide, 3-amino-4-methyl-6-phenyl-thieno[2,3-b]-pyridine-2-carboxamide, 3-amino-6-methyl-4-phenyl-thieno[2,3-b]pyridine-2-carboxylic acid amide, 3-amino-6-(4-bromo-phenyl)-4-methyl-thieno[2,3-b]pyridine-2-carboxylic acid amide, 3-amino-4-(4-bromo-phenyl)-6-methyl-thieno[2,3-b]pyridine-2-carboxylic acid amide, 3-amino-6-methyl-thieno[2,3-b]pyridine-2,4-dicarboxylic acid 2-amide 4-butylamide, 3-amino-6-furan-2-yl-4-phenyl-thieno[2,3-b]pyridine-2-carboxylic acid amide, 3-amino-6-furan-2-yl-4-pyridin-3-yl-thieno[2,3-b]pyridine-2-carboxylic acid amide, 3-amino-4-(4-chloro-phenyl)-6-phenyl-thieno[2,3-b]pyridine-2-carboxylic acid amide, 3-amino-4-(4-fluoro-phenyl)-6-furan-2-yl-thieno[2,3-b]pyridine-2-carboxylic acid amide, 3-amino-4-(4-chloro-phenyl)-6-furan-2-yl-thieno[2,3-b]pyridine-2-carboxylic acid amide, 3-amino-4-(4-bromo-phenyl)-6-furan-2-yl-thieno[2,3-b]pyridine-2-carboxylic acid amide, 3-amino-4,6-bis-(4-chloro-phenyl)-thieno[2,3-b]pyridine-2-carboxylic acid amide, 3-amino-6-naphth-2-yl-4-pyridin-3-yl-thieno[2,3-b]pyridine-2-carboxylic acid amide, 3-amino-6-methyl-thieno[2,3-b]pyridine-2,4-dicarboxylic acid 2-amide 4-(2-hydroxyethyl)amide, 3-amino-6-methyl-4-piperidin-1-yl-thieno[2,3-b]-pyridine-2-carboxamide and 3-amino-4-methyl-6-hydroxy-thieno[2,3-b]-pyridine-2-carboxamide reported as intermediates for synthesis of tricyclic heterocycles and evaluated for anti-allergic activity (G. Wagner et al., *Pharmazie*, 1990, 45, 102).

Other examples includes 3-amino-4,6-diphenyl-thieno[2,3-b]pyridine-2-carboxylic acid amide (A. M. Shestopalov et al., *J. Org. Chem. USSR*, (Engl. Transl.) 1984, 20, 1382), 3-amino-6-methyl-4-pyridin-4-yl-thieno[2,3-b]pyridine-2-carboxylic acid amide and 3-amino-6-methyl-4-pyridin-3-yl-thieno[2,3-b]pyridine-2-carboxylic acid amide (G. Wagner et al., *Pharmazie*, 1993, 48, 514), 3-amino-4-methoxymethyl-6-methyl-thieno[2,3-b]pyridine-2-carboxylic acid amide (E. I. Kaigorodova et al., *Chem. Heterocycl. Compd.* (*Engl. Transl.*), 1996, 32, 1234), 3-amino-6-phenyl-4-thiophen-2-yl-thieno[2,3-b]pyridine-2-carboxylic acid amide, 3-amino-4-furan-2-yl-6-methyl-thieno[2,3-b]pyridine-2-carboxylic acid amide, 3-amino-4-(4-chloro-phenyl)-6-methyl-thieno[2,3-b]pyridine-2-carboxylic acid amide and 3-amino-4-furan-2-yl-6-phenyl-thieno[2,3-b]pyridine-2-carboxylic acid amide (F. A. Attaby, *Phosphorus, Sulfur, Silicon Relat. Elem.*, 1998, 139, 1), 3-amino-6-(4-chloro-phenyl)-4-thiophen-2-yl-thieno[2,3-b]pyridine-2-carboxylic acid amide (Y. Sharanin et al., *J. Org. Chem. USSR*, (Engl. Transl.) 1996, 32, 1207), 3-amino-6-phenyl-4-pyridin-3-yl-thieno[2,3-b]pyridine-2-carboxylic acid amide (A. Krauze, *Eur. J. Med. Chem. Chim. Ther.*, 1999, 34, 301) and 3-amino-6-thiophen-2-yl-4-trifluoromethyl-thieno[2,3-b]pyridine-2-carboxylic acid amide (M. I. Abdel-Monem et al., *Pharmazie*, 2001, 56, 41).

U.S. Pat. Nos. 6,964,956 and 6,974,870 disclose substituted 3 amino-thieno[2,3-b]pyridine 2-carboxylic acid amide compounds and processes for their preparation.

SUMMARY OF THE INVENTION

It is therefore an object of this invention to provide novel compounds according to the following formula (I):

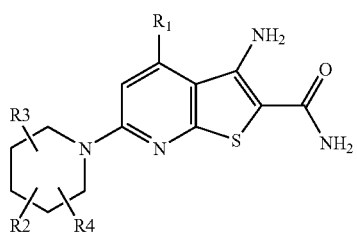

wherein the variables $R_1$, $R_2$, $R_3$ and $R_4$ are described herein which inhibit IKK. It is a further object of the invention to provide methods for treating diseases and pathological conditions exacerbated by IKK such as, but not limited to autoimmune diseases, inflammatory diseases, cardiovascular disease and cancer. It is yet a further object of the invention to provide novel processes for preparation of the above-mentioned novel compounds.

DETAILED DESCRIPTION OF THE INVENTION

A first aspect of the invention comprises a compound of formula (I):

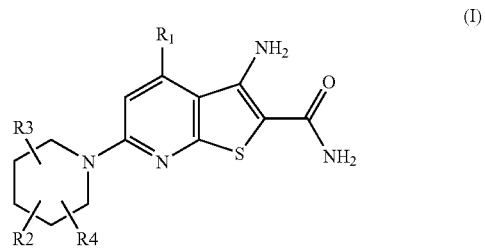

wherein:
$R_1$ is a partially halogenated $C_{1-6}$alkyl optionally substituted with one to two $R_5$,
$R_2$, $R_3$ and $R_4$ are independently selected from H, —S(O)$_n$ $C_{1-6}$alkyl, NR$_6$R$_7$, OH, CF$_3$ and $C_{1-6}$ alkyl;
$R_5$ is OH, CO$_2$H or $C_{1-6}$ alkoxy;
$R_6$ and $R_7$ are independently selected from H and $C_{1-6}$alkyl; and
n is 0, 1 or 2;
or a pharmaceutically acceptable salt thereof.

In its second aspect, the invention provides compounds of formula (I) as described above wherein:
$R_1$ is —CF$_2$H, —CF$_2$CH$_3$, —CF$_2$CH$_2$CH$_3$, —CF$_2$CH$_2$CH$_2$CH$_3$ or 1-fluoro-1-methyl ethyl;
$R_2$, $R_3$ and $R_4$ are independently selected from H, —S(O)$_n$ $C_{1-6}$alkyl, NR$_6$R$_7$, OH, CF$_3$ and $C_{1-6}$ alkyl;
$R_6$ and $R_7$ are independently selected from H and $C_{1-6}$alkyl;
n is 0, 1 or 2;
or a pharmaceutically acceptable salt thereof.

In a third embodiment, there are provided compounds of the formula (I) as described above wherein
$R_1$ is —CF$_2$H, —CF$_2$CH$_2$CH$_3$ or 1-fluoro-1-methyl ethyl;
$R_2$ and $R_3$ and $R_4$ are selected from H, and —S(O)$_n$C$_{1-6}$ alkyl; and
$R_6$, $R_7$ are independently selected from H and $C_{1-6}$alkyl;
n is 0, 1 or 2;
or the pharmaceutically acceptable salt thereof.

In a further embodiment of the invention, there are provided the following compounds:

TABLE I

| Compound | Name | Structure |
|---|---|---|
| 110 | 3-Amino-6-(4-amino-piperidin-1-yl)-4-(1,1-difluoro-propyl)-thieno[2,3-b]pyridine-2-carboxylic acid amide | 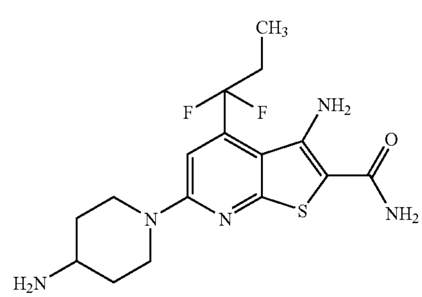 |

TABLE I-continued

| Compound | Name | Structure |
|---|---|---|
| 111 | 3-Amino-6-((S)-4-amino-3,3-dimethyl-piperidin-1-yl)-4-(1,1-difluoro-propyl)-thieno[2,3-b]pyridine-2-carboxylic acid amide | 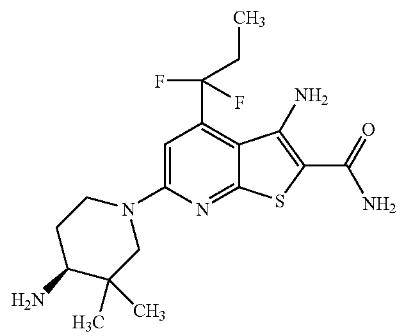 |
| 112 | 3-Amino-4-(1,1-difluoro-propyl)-6-(4-hydroxy-4-trifluoromethyl-piperidin-1-yl)-thieno[2,3-b]pyridine-2-carboxylic acid amide | 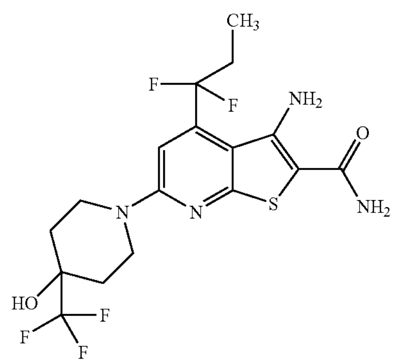 |
| 113 | 3-Amino-4-(1,1-difluoro-propyl)-6-(4-hydroxy-piperidin-1-yl)-thieno[2,3-b]pyridine-2-carboxylic acid amide | 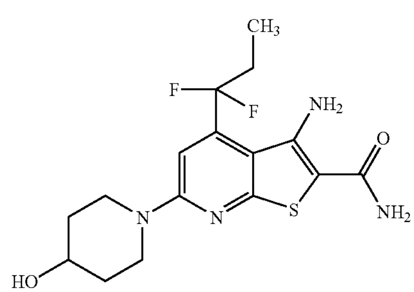 |
| 114 | 3-Amino-6-(4-amino-4-methyl-piperidin-1-yl)-4-(1,1-difluoro-propyl)-thieno[2,3-b]pyridine-2-carboxylic acid amide | 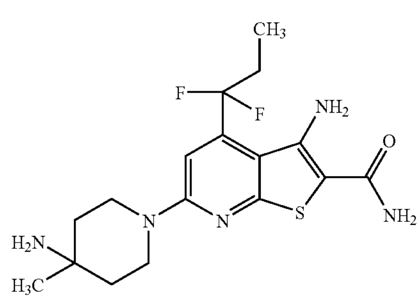 |

TABLE I-continued

| Compound | Name | Structure |
|---|---|---|
| 115 | 3-Amino-4-(1,1-difluoro-propyl)-6-(4-methanesulfonyl-piperidin-1-yl)-thieno[2,3-b]pyridine-2-carboxylic acid amide | 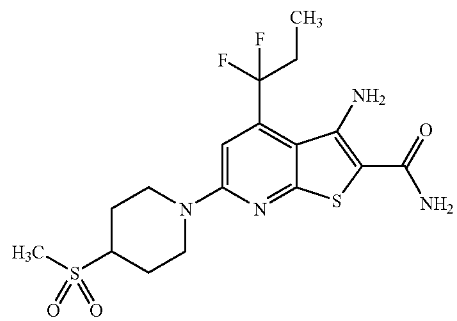 |
| 116 | 3-Amino-6-(4-amino-piperidin-1-yl)-4-difluoromethyl-thieno[2,3-b]pyridine-2-carboxylic acid amide | 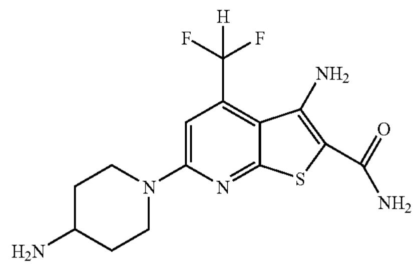 |
| 117 | 3-Amino-4-difluoromethyl-6-(4-hydroxy-piperidin-1-yl)-thieno[2,3-b]pyridine-2-carboxylic acid amide | 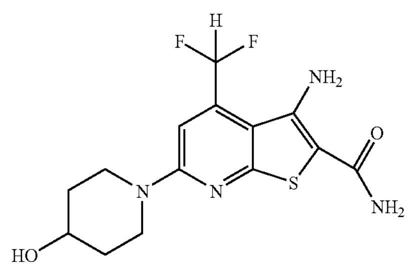 |
| 118 | 3-Amino-4-(1-fluoro-1-methyl-ethyl)-6-(4-methanesulfonyl-piperidin-1-yl)-thieno[2,3-b]pyridine-2-carboxylic acid amide | 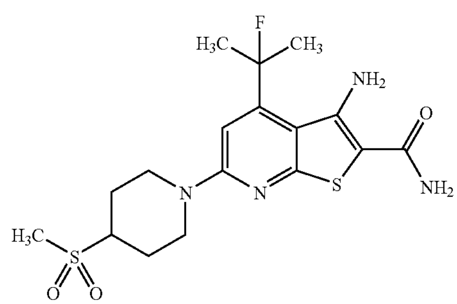 |
| 119 | 3-Amino-4-(1,1-difluoro-propyl)-6-(4-hydroxy-4-methyl-piperidin-1-yl)-thieno[2,3-b]pyridine-2-carboxylic acid amide | 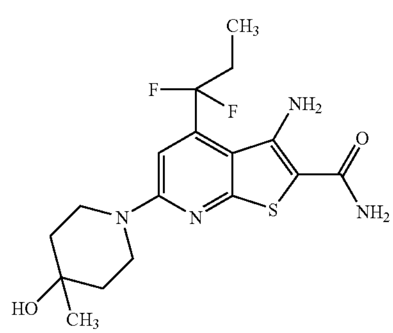 |

TABLE I-continued

| Compound | Name | Structure |
|---|---|---|
| 120 | 3-Amino-4-(1,1-difluoro-propyl)-6-(4-hydroxy-3,3-dimethyl-piperidin-1-yl)-thieno[2,3-b]pyridine-2-carboxylic acid amide | 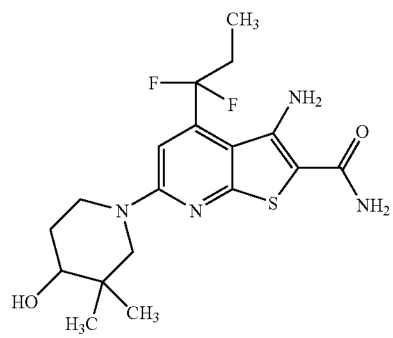 |
| 121 | 3-Amino-4-difluoromethyl-6-(4-methylamino-piperidin-1-yl)-thieno[2,3-b]pyridine-2-carboxylic acid amide | | or the pharmaceutically acceptable salt thereof.

Another embodiment of the invention provides a method of treating inflammatory and autoimmune conditions said method comprising administering to a patient in need of such treatment a therapeutically effective amount of a compound according to formula (I) as defined herein or a pharmaceutically acceptable salt thereof.

Another embodiment of the invention provides a method of treating inflammatory or autoimmune diseases or conditions, said method comprised of the step of administering to a patient in need thereof a therapeutically effective amount of a compound according to Formula I.

Another embodiment of the invention provides a method of treating inflammatory or autoimmune diseases or conditions wherein said diseases or conditions are selected from the list consisting of osteoarthritis, reperfusion injury, asthma, multiple sclerosis, Gillian-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitis, acute and chronic pain, thermal injury, adult respiratory distress syndrome (ARDS), chronic obstructive pulmonary disease (COPD), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis and wherein said method is comprised of the step of administering to a patient in need thereof a therapeutically effective amount of a compound according to formula (I) as defined herein or a pharmaceutically acceptable salt thereof.

Another embodiment of the invention provides a method of treating cancer conditions wherein said method is comprised of the step of administering to a patient in need thereof a therapeutically effective amount of a compound according to formula I.

Another embodiment of the invention provides a method for treating cancer conditions wherein said method is comprised of the step of administering to a patient in need thereof a therapeutically effective amount of a compound according to formula I, and wherein said cancer condition is selected from the list consisting of lymphoid-, myeloid- and epithelial-derived malignancies, leukemia, lymphomas, breast cancer, gastric cancer, colorectal cancer, lung cancer, and pancreatic cancer, wherein said method is comprised of the step of administering to a patient in need thereof a therapeutically effective amount of a compound according to formula (I) as defined herein or a pharmaceutically acceptable salt thereof.

A recent review describes the essential role of inflammatory mediators in the development of cardiovascular disease. The inflammatory mediators and the cells that they recruit are reported to play a key role in the development of fatty streaks and plaques that lead to atherosclerosis. In addition they are reported to play a key role in subsequent degradation of the fibrous cap that forms over the plaque, leading to rupture and clot formation. If the clot grows large enough it can lead to myocardial infarction or stroke. Thus, anti-inflammatory drugs that can inhibit the production of these mediators and subsequent recruitment and activation of these cells may be beneficial in treatment of these diseases (P. Libby, *Scientific American*, 2002, 46).

The invention also provides methods for making compounds according to general formula (I) as described herein.

EXAMPLES

Compounds according to the invention demonstrate good oral exposure and in vitro potency.

Example 1

Benefit of Halogenated Propyl at the R1 Position Relative to Other Compounds

TABLE II

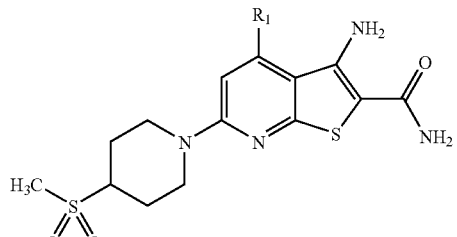

Compounds 100, 101 and 115

| R1 = | n-propyl | —CF$_3$ | —CF$_2$CH$_2$CH$_3$ |
|---|---|---|---|
| Compound | Compound 100 | Compound 101 | Compound 115 |
| Molecular assay IKKb (µM) | 0.078 | 0.12 | 0.026 |
| Cell assay HeLa (µM) | 0.72 | 3.2 | 0.7 |
| Rat oral exposure (µM) @ | | | |

TABLE II-continued

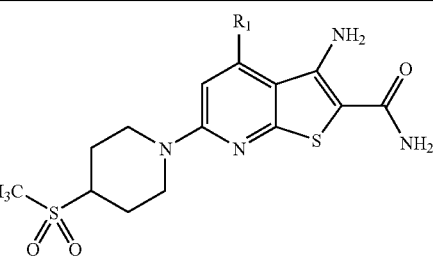

Compounds 100, 101 and 115

| R1 = | n-propyl | —CF$_3$ | —CF$_2$CH$_2$CH$_3$ |
|---|---|---|---|
| 10 mg/kg dose | | | |
| 2h | 0.21 | Not tested | 1.59 |
| 6h | 0.12 | Not tested | 0.78 |
| 10h | 0.08 | Not tested | 0.65 |

Table II shows that when used in combination with the left hand side 4-methylsulfonyl piperidine group (compounds of the invention wherein $R_2$ and $R_3$=H, $R_4$=4-methylsulfonyl), 1,1-difluoropropyl and n-propyl $R_1$ groups of compounds 115 and 100, respectively, confer improved cellular potency relative to the —CF$_3$ group of compound 101. The combination of the left hand side 4-methylsulfonyl piperidine group with the -1,1-difluoropropyl group in Compound 115 further distinguishes itself from Compound 100 by its improved level of sustained plasma exposure upon oral administration to rat.

Example 2

Comparison of In Vivo Activity in Rat CIA Model Between Compound 115 and Other Analogs

TABLE III

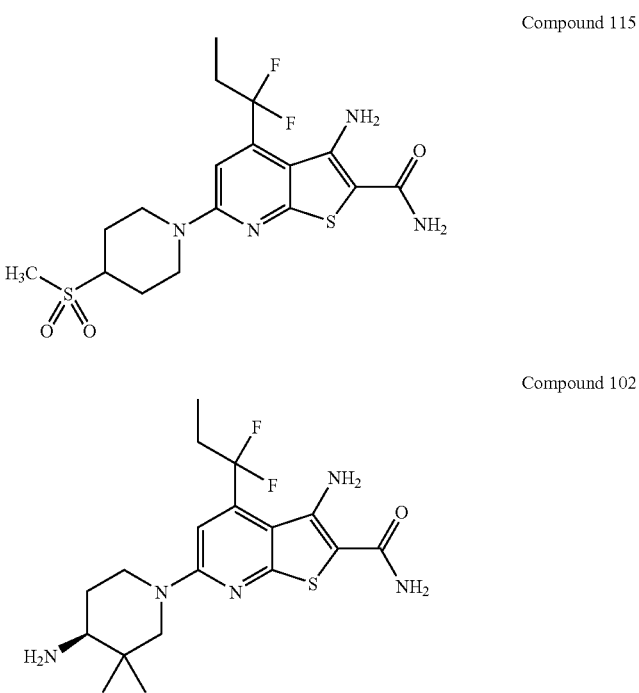

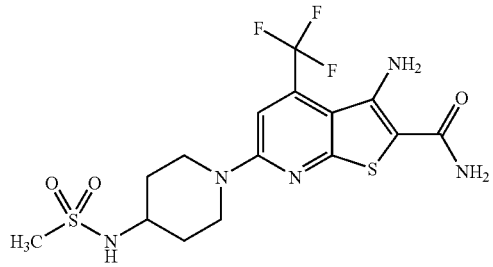

Compound 103

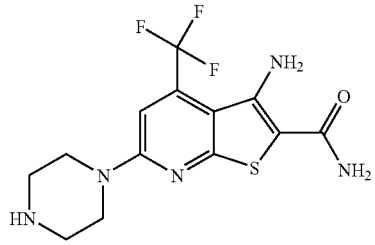

Compound 104

| Compound | 115 | 102 | 103 | 104 |
|---|---|---|---|---|
| Dose | 10 mg/kg BID | 10 mg/kg BID | 30 mg/kg BID | 30 mg/kg BID |
| Inhibition of paw weight increase | 44% | not statistically significant | not statistically significant | not statistically significant |

Compound 115 demonstrates superior oral activity in a rat model of collagen induced arthritis.

For all the compounds disclosed in this application, in the event the nomenclature is in conflict with the structure, it shall be understood that the compound is defined by the structure.

The invention includes pharmaceutically acceptable derivatives of compounds of formula (I). A "pharmaceutically acceptable derivative" refers to any pharmaceutically acceptable acid, salt or ester of a compound of this invention, or any other compound which, upon administration to a patient, is capable of providing (directly or indirectly) a compound of this invention, a pharmacologically active metabolite or pharmacologically active residue thereof.

Pharmaceutically acceptable salts of the compounds of this invention include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds of this invention and their pharmaceutically acceptable acid addition salts. Salts derived from appropriate bases include alkali metal (e.g., sodium), alkaline earth metal (e.g., magnesium), ammonium and $N-(C_1-C_4\ alkyl)_4^+$ salts.

In addition, the compounds of this invention include prodrugs of compounds of the formula (I). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (I), thereby imparting the desired pharmacological effect.

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

The compounds of the invention are only those which are contemplated to be 'chemically stable' as will be appreciated by those skilled in the art. For example, a compound which would have a 'dangling valency', or a 'carbanion' are not compounds contemplated by the invention.

As used herein, the following abbreviations are used:

DMF is dimethylformamide;

EtOH is ethanol;

HPLC is high-performance liquid chromatography

THF is tetrahydrofuran;

TLC is thin layer chromatography

Terms not specifically defined herein should be given the meanings that would be given to them by one of skill in the art in light of the disclosure and the context. For example, "$C_{1-6}$alkoxy" is a $C_{1-6}$alkyl with a terminal oxygen, such as methoxy, ethoxy, propoxy, pentoxy and hexoxy. All alkyl, alkylene or alkynyl groups shall be understood as being branched, unbranched unless otherwise specified. Other more specific definitions are as follows:

The term "alkyl" refers to a saturated aliphatic radical containing from one to ten carbon atoms or a mono- or polyunsaturated aliphatic hydrocarbon radical containing from two to twelve carbon atoms unless otherwise stated. The mono- or polyunsaturated aliphatic hydrocarbon radical contains at least one double or triple bond, respectively. "Alkyl" refers to both branched and unbranched alkyl groups. Examples of "alkyl" include alkyl groups which are straight chain alkyl groups containing from one to eight carbon atoms and branched alkyl groups containing from three to ten carbon atoms. Other examples include lower alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group ($C=O$). Each alkyl or alkyl analog described herein shall be understood to be optionally partially or fully halogenated.

The term "halogen" refers to bromine, chlorine, fluorine or iodine.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, if a substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Such combinations of substituents and/or variables, however, are permissible only if such combinations result in stable compounds.

As used herein above and throughout this application, "nitrogen" and "sulfur" include any oxidized form of nitrogen and sulfur and the quaternized form of any basic nitrogen.

Methods of Therapeutic Use

In accordance with the invention, there are provided novel methods of using the compounds of the formula (I). The compounds of the invention are effective in inhibiting the activity of IKKβ and/or IKKα. In particular, these compounds are useful in blocking disease processes exacerbated by IKKβ-mediated NF-κB activation and IKKα activation of B cell activity or the cell cycle regulatory gene Cyclin D1. In blocking NF-κB activation, compounds of the invention effectively block transcription of genes encoding inflammatory cytokines including IL-1, IL-2, IL-6, IL-8, TNFα, chemokines including IL-8 and RANTES as well as other pro-inflammatory molecules including COX-2 and cell adhesion molecules such as ICAM-1, VCAM-1 and E-selectin. These mediators play a key role in the etiology of inflammatory, autoimmune and cardiovascular disorders and cancer. Preventing the production of these mediators is a desirable means for treating these disorders. Thus there are provided methods for treating these conditions using the compounds of the invention. Such inflammatory and autoimmune conditions include but are not limited to osteoarthritis, reperfusion injury, asthma, chronic obstructive pulmonary disease (COPD), multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitus, acute and chronic pain, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis. Such cardiovascular disorders include but are not limited to atherosclerosis, myocardial infarction and stroke. Such cancers include but are not limited to lymphoid-, myeloid- and epithelial-derived malignancies including leukemia, lymphomas and breast, gastric, colorectal, lung, and pancreatic cancers. The compounds of the invention can also be used to treat other disorders associated with IKK activation of NF-κB unrelated to those listed above or discussed in the Background of the Invention. For example, the compounds of the invention may also be useful in the treatment of cancer by enhancing the effectiveness of chemotherapeutic agents. Therefore, the invention also provides methods of treating inflammatory and autoimmune diseases, and other diseases including cancer, comprising administering to a patient in need of such treatment a pharmaceutically effect amount of a compound according to the invention.

For therapeutic use, the compounds of the invention may be administered in any conventional dosage form in any conventional manner. Routes of administration include, but are not limited to, intravenously, intramuscularly, subcutaneously, intrasynovially, by infusion, sublingually, transdermally, orally, topically or by inhalation. The preferred modes of administration are oral and intravenous. Compositions comprising the compounds of the invention for each of the aforementioned routes of administration will be apparent to the skilled artisan. The invention also provides for pharmaceutical compositions including a therapeutically effective amount of the compounds according to the invention. Such pharmaceutical compositions will include pharmaceutically acceptable carriers and adjuvants as further described below.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime. The compounds of this invention may be used in combination with other inflammatory agents such as methotrexate or low dose steroids.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

Synthetic Methods

The invention additionally provides for methods for making the compounds of formula (I). The compounds of the invention may be prepared by the general methods and examples presented below and methods known to those of ordinary skill in the art. Methods of making substituted 3 amino-thieno[2,3-b]pyridine 2-carboxylic acid amides compounds are also disclosed in U.S. Pat. No. 6,964,956 and U.S. Pat. No. 6,974,870 the contents of which are incorporated herein in their entirety. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC). Intermediates and products may be purified by methods known in the art, including column chromatography, HPLC or recrystallization.

As illustrated in Scheme I, compounds of formula (I) may be prepared starting with a 1,3-dione bearing substituents $R_1$ and R' (II). Reaction of (II) with cyanothioacetamide (III) in a suitable solvent such as EtOH, in the presence of a suitable base such as triethylamine provides the substituted 2-mercaptonicotinonitrile (IV). Reaction of (IV) with chloro- or bromoacetamide (V), in a suitable solvent such as DMF, THF or EtOH, in the presence of a suitable base such as sodium carbonate, sodium hydroxide or sodium ethoxide, provides the desired compound of formula (I). Substituents $R_1$ and R' may be further modified by methods known in the art to produce additional compounds of the invention.

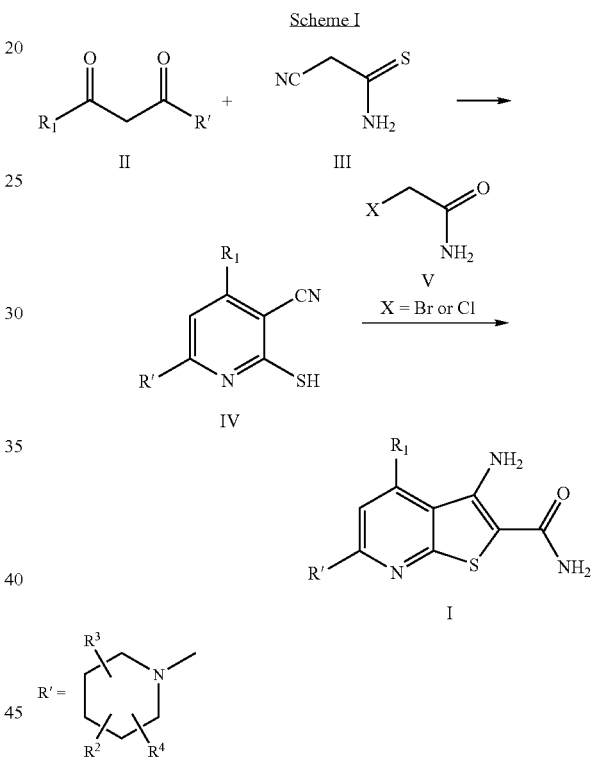

An alternate procedure for preparing compounds of formula (I) is illustrated in Scheme II. An alkynoate ester, such as the methyl ester shown, is reacted with 2-cyanothioacetamide in the presence of a suitable base such as morpholine in a suitable solvent such as ethanol to provide (VI). Treatment of (VI) with 2-chloro or 2-bromo acetamide in the presence of a suitable base such as NaH in a suitable solvent such as DMF provides (VII). Reaction of (VII) with a suitable sulfonating reagent such as N-phenyltrifluoromethane-sulfonimide in the presence of a suitable base such as diisopropylethylamine in a suitable solvent such as dioxane provides the sulfonyl ester (VIII) (R'=CF$_3$ in this case). Alternately, a halogen may be used as a leaving group instead of the sulfonyl ester. For example, one may treat (VII) with a chlorinating agent such as POCl$_3$ to prepare the chloro compound. Reaction of (VIII) with the desired nucleophile, such as an amine in the presence of a suitable base such as triethylamine, optionally while heating at about 50° C. to 100° C. results in displacement of the sulfonyl ester by the nucleophile. Cyclization in situ may be achieved by adding a second suitable base such as aqueous sodium carbonate followed by continued heating to provide the desired compound of formula (I).

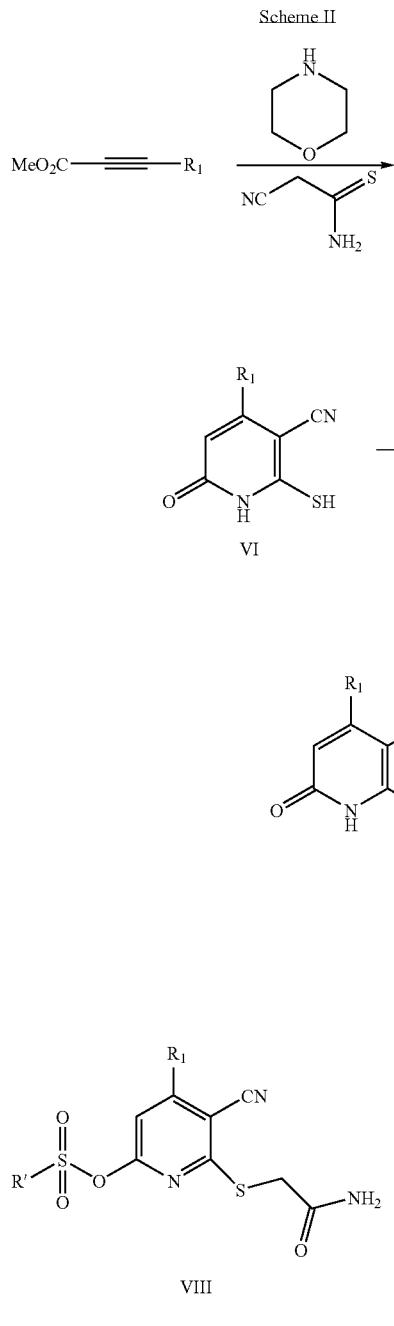

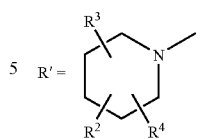

Compounds of formula (I) may also be prepared in a variation of this approach shown in Scheme III. In this method cyclization of the alkynyl ester with 2-cyano acetamide, in place of 2-cyano thioacetamide, in the presence of potassium hydroxide in ethanol at room temperature provides the alkali salt of the corresponding hydroxyl pyridine (IX). Heating this material with tetramethyl ammonium chloride in refluxing phosphorous oxychloride provides the intermediate 4-substituted 2,6-dichloro-3-cyano pyridine (X) which is further converted to (I) by an SNAR reaction with a nucleophilic heterocycle to introduce the R' group followed by addition of 2-mercapto acetamide and subsequent intramolecular cyclization to form the desired compound of formula (I).

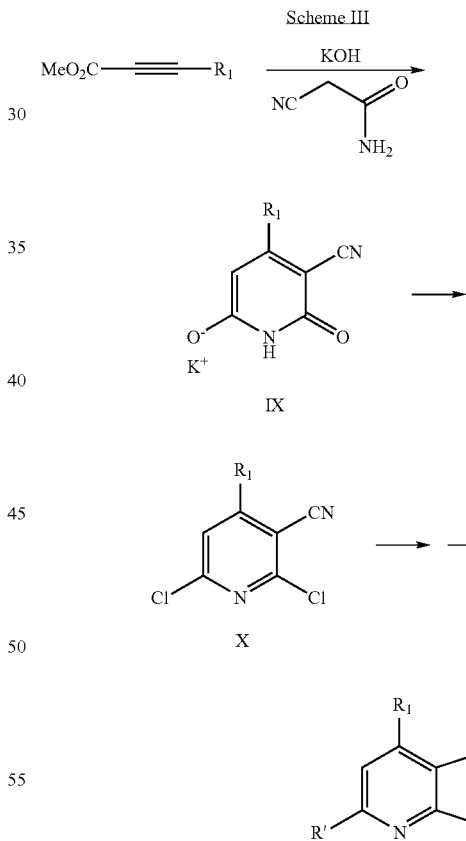

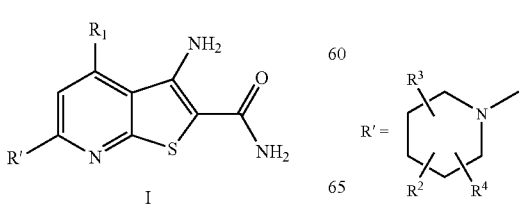

SYNTHETIC EXAMPLES

Example A

3-Amino-4-(1,1-difluoro-propyl)-6-(4-methanesulfonyl-piperidin-1-yl)-thieno[2,3-b]pyridine-2-carboxylic acid amide

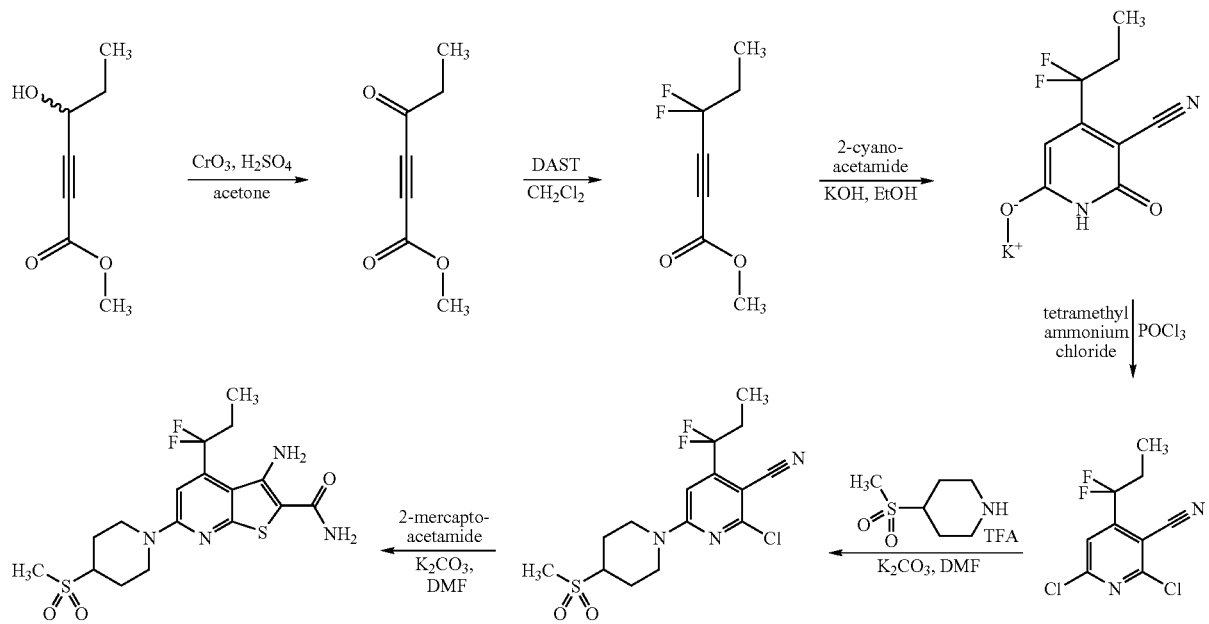

To a solution of methyl-4-hydroxy-2-hexynoate (25.0 g, 176 mmol) in acetone (200 mL), cooled in an ice water bath, was added Jones reagent (70 mL of 3.2 M chromium VI oxide in 1:3 sulfuric acid:water). The reaction mixture was allowed to stir at room temperature for 3 h then filtered through a plug of diatomaceous earth and the filter cake was rinsed with dichloromethane (2×100 mL). The organic phase was saved and the aqueous phase was extracted with dichloromethane (2×100 mL). The combined organic phases were washed with saturated sodium bicarbonate (2×200 mL), dried (sodium sulfate) and concentrated to provide 17.0 g (69%) of 4-oxo-hex-2-ynoic acid methyl ester.

A solution of the above methyl ester (8.5 g, 61 mmol) in dichloromethane (200 mL) was treated with diethylaminosulfurtrifluoride (DAST) (25.0 mL, mmol) and the reaction mixture was stirred overnight at room temperature. The reaction mixture was transferred into a 500 mL separatory funnel and cautiously added dropwise to a beaker of crushed ice (300 g) to avoid exothermic decomposition of the DAST reagent. After the ice had melted, the phases were separated and the aqueous phase was extracted with dichloromethane (100 mL). The combined organic phases were dried (magnesium sulfate) and concentrated on a rotary evaporator to provide 9.5 g (97%) of 4,4-difluoro-hex-2-ynoic acid methyl ester as a dark red oil.

Potassium hydroxide pellets (7.3 g, 130 mmol) were added to a solution of the above ester (19 g, 117 mmol) and 2-cyanoacetamide (10.0 g, 119 mmol) in ethanol (325 mL). The reaction mixture was allowed to stir overnight at room temperature then filtered to provide 23.0 g (78%) of the potassium salt of 4-(1,1-difluoro-propyl)-6-hydroxy-2-oxo-1,2-dihydro-pyridine-3-carbonitrile as a light pink solid.

A suspension of the above carbonitrile (7.2 g, 28.5 mmol) and tetramethyl ammonium chloride (6.6 g, 60.2 mmol) in phosphorous oxychloride (50 mL) was heated in a sealed tube at 110° C. for 18 h. The reaction mixture was then cooled to room temperature, poured over crushed ice, and stirred for 20 min. The resulting precipitate was isolated by filtration. This material was taken up in a minimum amount of 10% ethyl acetate in hexanes and vacuum filtered through a plug of silica gel using 10% ethyl acetate in hexanes as the mobile phase. Concentration provided 6.0 g (87%) of 2,6-dichloro-4-(1,1-difluoro-propyl)-nicotinonitrile as a light tan solid.

A suspension of 4-(methylsulfonyl)piperidine trifluoroacetate (2.08 g, 7.5 mmol), the above nicotinonitrile (1.88 g, 7.5 mmol), and potassium carbonate (5.18 g, 37.5 mmol) in DMF (20 mL) was stirred at room temperature overnight. The reaction mixture was then diluted with additional DMF (20 mL) and purged with nitrogen as 2-mercaptoacetamide was added (7.5 mmol as a 2M solution in methanol). After stirring for 3 h at room temperature the reaction mixture was heated to 80° C. overnight to affect the intramolecular thiopene cyclization reaction. The dark colored reaction was then poured into water, filtered, and washed with additional water to provide 2.24 g (69%) of the title compound as a yellow-brown solid; calculated for $C_{17}H_{22}F_2N_4O_3S_2$ 432.51, see desired MH+ of 433.38 m/z.

Example B

3-Amino-4-difluoromethyl-6-(4-methylamino-piperidin-1-yl)-thieno[2,3-b]pyridine-2-carboxylic acid amide

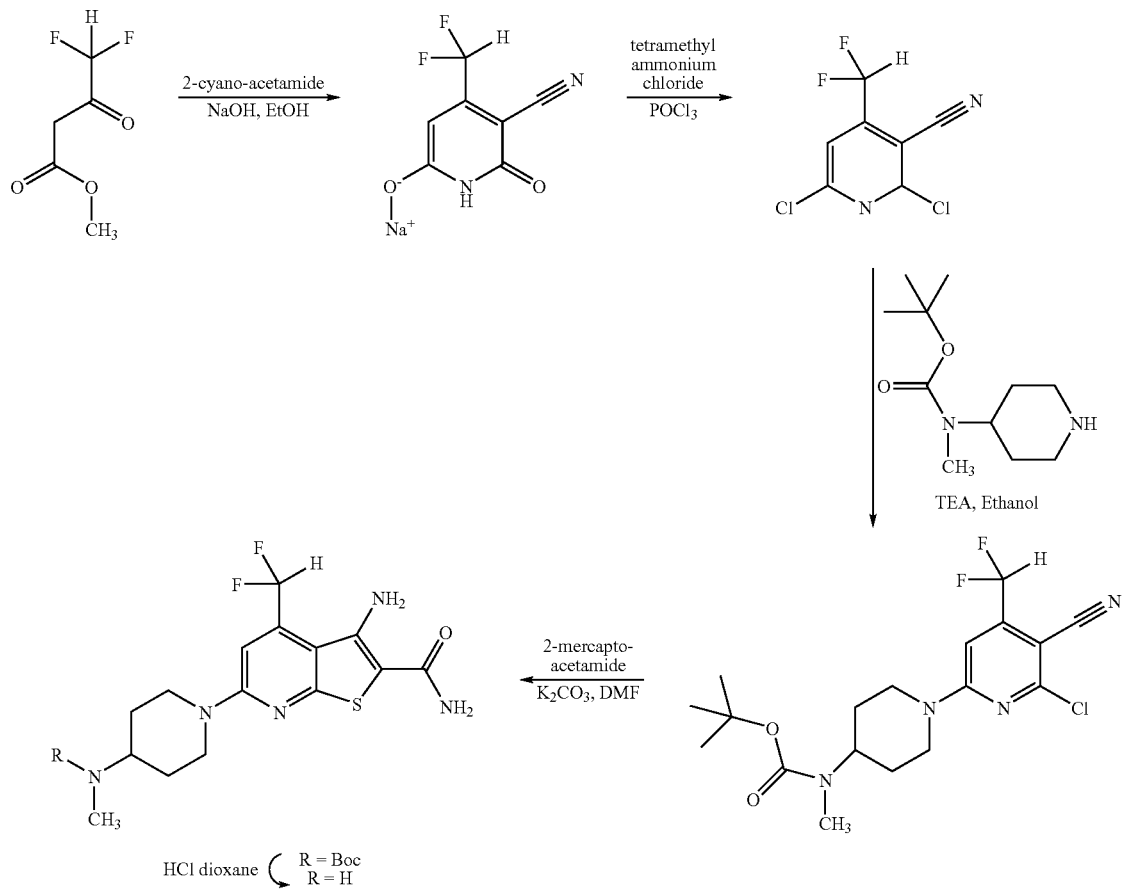

Sodium hydroxide pellets (6.0 g, 150 mmol) were added to a solution of ethyl-4,4-difluoroacetate (25.0 g, 143 mmol) and 2-cyanoacetamide (12.0 g, 143 mmol) in ethanol (180 mL). The reaction mixture was stirred at room temperature for 45 h, then filtered to provide 24.7 g (83%) of the sodium salt of 4-difluoromethyl-6-hydroxy-2-oxo-1,2-dihydro-pyridine-3-carbonitrile as a tan solid.

A suspension of the above carbonitrile (5.0 g, 24.0 mmol) and tetramethyl ammonium chloride (3.2 g, 29.2 mmol) in phosphorous oxychloride (10 mL) was heated in a sealed tube at 145° C. for 20 h. The reaction mixture was then cooled to room temperature, poured over crushed ice, and stirred for 2 h. The resulting precipitate was isolated by filtration. This material was taken up in ethyl acetate (250 mL), dried (magnesium sulfate), and concentrated to provide 4.1 g (77%) of 2,6-dichloro-4-difluoromethyl-nicotinonitrile as a brown solid. This material was used without further purification.

A solution of the above nicotinonitrile (2.4 g, 10.8 mmol) in ethanol (40 mL) was cooled in a dry ice/acetone bath. Triethylamine (1.5 mL, 11.0 mmol) and N-methyl, N-boc-4-aminopiperidine were added and the reaction mixture was allowed to warm gradually to room temperature overnight. The reaction was concentrated, taken up in ethyl acetate (200 mL) and washed with 1 N HCl (2×100 mL). The organic phase was dried (magnesium sulfate) and concentrated to provide a 4 to 1 mixture of addition products to the 6 and 2 position, respectively. These regioisomers were separated by silica gel chromatography using a gradient of ethyl acetate in hexanes as the mobile phase to provide 1.3 g (30%) of (6'-chloro-5'-cyano-4'-difluoromethyl-3,4,5,6-tetrahydro-2H-[1,2']bipyridinyl-4-yl)-methyl-carbamic acid tert-butyl ester as a white solid.

A suspension of (6'-chloro-5'-cyano-4'-difluoromethyl-3,4,5,6-tetrahydro-2H-[1,2']bipyridinyl-4-yl)-methyl-carbamic acid tert-butyl ester (1.1 g, 2.74 mmol) potassium carbonate (1.9 g, 13.7 mmol) in DMF (15 mL) was treated with 2-mercaptoacetamide (solution of 1 g, 11 mmol in 10 mL of methanol), and the reaction mixture was heated in a sealed tube at 80° C. overnight. The reaction mixture was then cooled to room temperature and filtered. The filtrate was treated with water (50 mL) and the resulting precipitate was collected by filtration to provide 1.03 g (82.4%) of [1-(3-amino-2-carbamoyl-4-difluoromethyl-thieno[2,3-b]pyridin-6-yl)-piperidin-4-yl]-methyl-carbamic acid tert-butyl ester as a tan solid.

A suspension of the above tert-butyl ester intermediate (600 mg, 1.32 mmol) in dichloromethane (10 mL) was treated with HCl (4 N solution in dioxane, 3.5 mL, 14 mmol)/The reaction mixture was stirred at room temperature for 10 h, then concentrated to dryness on a rotary evaporator. The resulting residue was washed with 2 N sodium carbonate, rinsed with water, and air dried to provide 370 mg (79%) of the title compound, as a tan solid; calculated for $C_{15}H_{19}F_2N_5OS$ 355.41, see desired MH+ of 356.34 m/z.

Example C 2,6-Dichloro-4-(1-fluoro-1-methyl-ethyl)-nicotinonitrile

To a solution of the above ethyl ester (7.5 g, 31.2 mmol) in methanol (250 mL) was added concentrated hydrochloric acid (0.05 mL, 0.6 mmol). The reaction mixture was stirred at room temperature for 15 h then concentrated, diluted with water, and extracted with ethyl acetate. The combined organic phases were dried (sodium sulfate), and concentrated to provide 4.9 g (100%) of 4-hydroxy-4-methyl-pent-2-ynoic acid ethyl ester as a clear oil.

A solution of 4-hydroxy-4-methyl-pent-2-ynoic acid ethyl ester (4.9 g, 155 mmol) in dichloromethane (30 mL) was cooled to −78° C. and treated with DAST (5.3 g, 161.2 mmol) the reaction mixture was stirred for 2 h at −78° C. then warmed to room temperature and poured over ice. After the

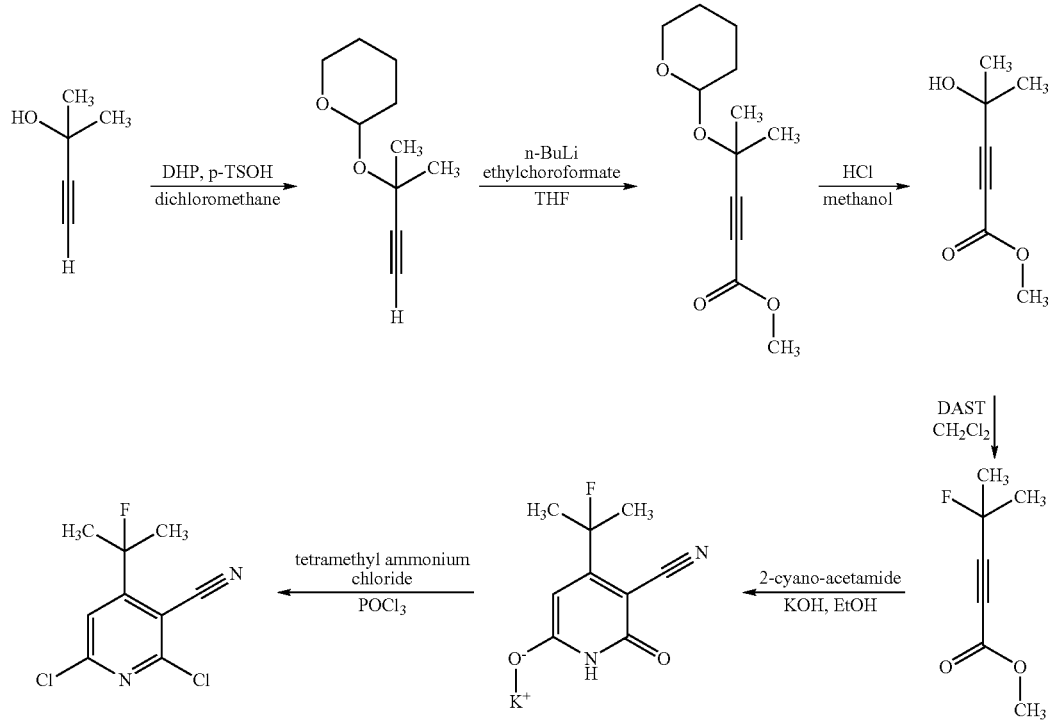

To a solution of 2-methyl-3-butyn-2-ol (17.0 g, 202.1 mmol) in dichloromethane (200 mL) cooled to 0° C. was added 2,3-dihydropyran (22.0 mL, 258.4 mmol), followed by para-toluenesulfonic acid (10 mg, 0.05 mmol). The mixture was allowed to slowly warm to room temperature over 3 h, then washed with a saturated aqueous solution of sodium bicarbonate, followed by brine, then dried (sodium sulfate), and concentrated to provide 34.0 g (97%) of 2-(1,1-dimethyl-prop-2-ynyloxy)-tetrahydropyran as a clear oil.

To a solution of 2-(1,1-dimethyl-prop-2-ynyloxy)-tetrahydropyran (10.0 g, 59.4 mmol) in THF (100 mL), cooled to −78° C. was added n-butyl lithium (26 mL, 65 mmol) as a solution in hexanes. The mixture was stirred at −78° C. for 1 h then a solution of ethyl chloroformate (7.0 mL, 108.5 mmol) in THF (100 mL) was added dropwise. The mixture was stirred at −78° C. for 1 h then quenched by addition of a saturated aqueous solution of ammonium chloride. This mixture was diluted with water and extracted with ethyl acetate. The organic phase was dried (sodium sulfate) and concentrated to provide 7.5 g (53%) of 4-methyl-4-(tetrahydro-pyran-2-yloxy)-pent-2-ynoic acid ethyl ester as a clear oil.

ice had melted, the phases were separated and the aqueous phase was extracted with dichloromethane. The combined organic phases were dried (sodium sulfate) and concentrated on a rotary evaporator to provide 5.0 g (100%) of 4-fluoro-4-methyl-pent-2-ynoic acid ethyl ester as a brown oil.

Potassium hydroxide pellets (2.0 g, 35.6 mmol) were added to a solution of 4-fluoro-4-methyl-pent-2-ynoic acid ethyl ester (5.2 g, 33 mmol) and 2-cyanoacetamide (2.8 g, 33.3 mmol) in ethanol (35 mL). The reaction mixture was allowed to stir for 2 h then filtered to provide 3.7 g (48%) of the potassium salt of 4-(1-fluoro-1-methyl-ethyl)-6-hydroxy-2-oxo-1,2-dihydro-pyridine-3-carbonitrile as a tan solid.

A suspension of the above carbonitrile (3.7 g, 15.8 mmol) and tetramethyl ammonium chloride (3.5 g, 31.9 mmol) in phosphorous oxychloride (30 mL) was heated in a sealed tube at 110° C. for 15 h. The reaction mixture was then cooled to room temperature, poured over crushed ice, and stirred until all the ice had melted. The resulting precipitate was isolated by filtration. This material was taken up in a minimum amount of 10% ethyl acetate in hexanes and vacuum filtered through a plug of silica gel using 10% ethyl acetate in hexanes as the mobile phase. Concentration provided 2.1 g (57%) of 2,6-dichloro-4-(1-fluoro-1-methyl-ethyl)-nicotinonitrile as a white solid.

The following compounds were also prepared by the methods described in the above Examples:

3-Amino-6-(4-amino-piperidin-1-yl)-4-(1,1-difluoro-propyl)-thieno[2,3-b]pyridine-2-carboxylic acid amide

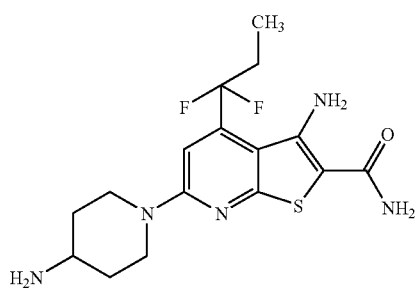

Prepared in analogous fashion to Example 1 using 4-aminopiperidine in place of 4-(methylsulfonyl)piperidine; calculated for $C_{16}H_{21}F_2N_5OS$ 369.43, see desired MH+ of 370.05 m/z.

3-Amino-4-(1,1-difluoro-propyl)-6-(4-hydroxy-4-methyl-piperidin-1-yl)-thieno[2,3-b]pyridine-2-carboxylic acid amide

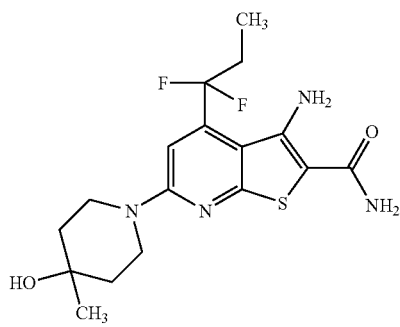

Prepared in analogous fashion to Example 1 using 4-hydroxy-4-methyl-piperidine in place of 4-(methylsulfonyl)piperidine; calculated for $C_{17}H_{22}F_2N_4O_2S$ 384.45, see desired MH+ of 385.55 m/z.

3-Amino-4-(1,1-difluoro-propyl)-6-(4-hydroxy-3,3-dimethyl-piperidin-1-yl)-thieno[2,3-b]pyridine-2-carboxylic acid amide

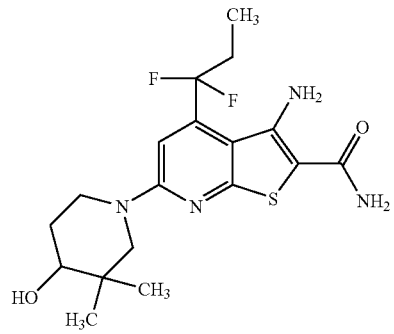

Prepared in analogous fashion to Example 1 using 4-hydroxy-3,3-dimethyl-piperidine in place of 4-(methylsulfonyl)piperidine; calculated for $C_{18}H_{24}F_2N_4O_2S$ 398.47, see desired MH+ of 399.55 m/z.

3-Amino-6-((S)-4-amino-3,3-dimethyl-piperidin-1-yl)-4-(1,1-difluoro-propyl)-thieno[2,3-b]pyridine-2-carboxylic acid amide

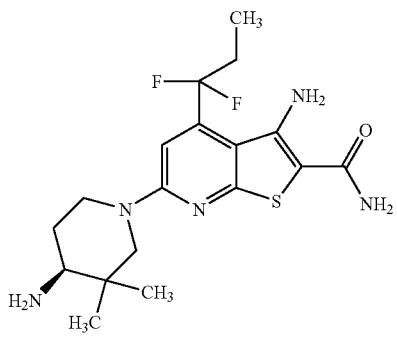

Prepared in analogous fashion to Example 1 using (S)-4-amino-3,3-dimethyl-piperidine in place of 4-(methylsulfonyl)piperidine; calculated for $C_{18}H_{25}F_2N_5OS$ 397.49, see desired MH+ of 398.60 m/z.

3-Amino-4-(1,1-difluoro-propyl)-6-(4-hydroxy-4-trifluoromethyl-piperidin-1-yl)-thieno[2,3-b]pyridine-2-carboxylic acid amide

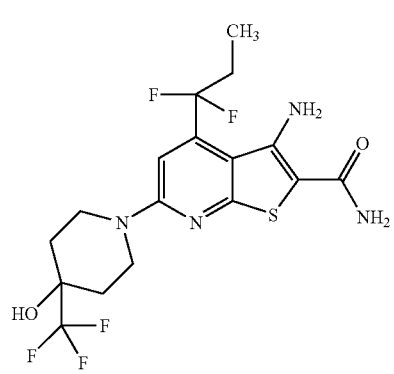

Prepared in analogous fashion to Example 1 using 4-hydroxy-4-trifluoromethyl-piperidine in place of 4-(Methylsulfonyl)piperidine; calculated for $C_{17}H_{19}F_5N_4O_2S$ 438.42, see desired MH+ of 438.88 m/z.

3-Amino-4-(1,1-difluoro-propyl)-6-(4-hydroxy-piperidin-1-yl)-thieno[2,3-b]pyridine-2-carboxylic acid amide

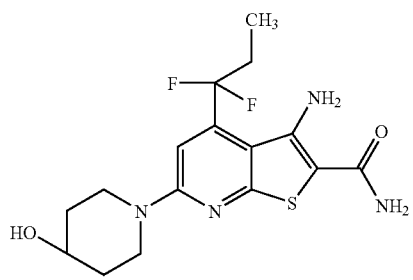

Prepared in analogous fashion to Example 1 using 4-hydroxypiperidine in place of 4-(methylsulfonyl)piperidine; calculated for $C_{16}H_{20}F_2N_4O_2S$ 370.42, see desired MH+ of 371.52 m/z.

3-Amino-6-(4-amino-4-methyl-piperidin-1-yl)-4-(1,1-difluoro-propyl)-thieno[2,3-b]pyridine-2-carboxylic acid amide

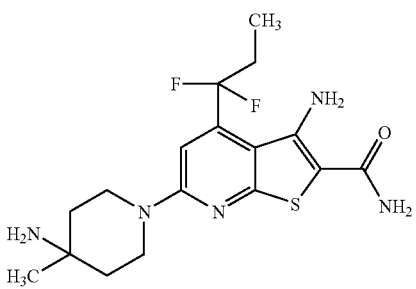

Prepared in analogous fashion to Example 1 using 4-amino-4-methylpiperidine in place of 4-(methylsulfonyl)piperidine; calculated for $C_{17}H_{23}F_2N_5OS$ 383.46, see desired MH+ of 384.34 m/z.

3-Amino-6-(4-amino-piperidin-1-yl)-4-difluoromethyl-thieno[2,3-b]pyridine-2-carboxylic acid amide

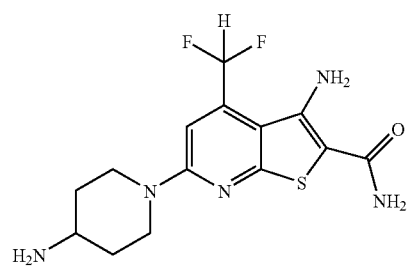

Prepared in analogous fashion to Example 2 using 4-aminopiperidine in place of 4-(N-methyl, N-Boc)aminopiperidine; calculated for $C_{14}H_{17}F_2N_5OS$ 341.38, see desired MH+ of 342.55 m/z.

3-Amino-4-difluoromethyl-6-(4-hydroxy-piperidin-1-yl)-thieno[2,3-b]pyridine-2-carboxylic acid amide

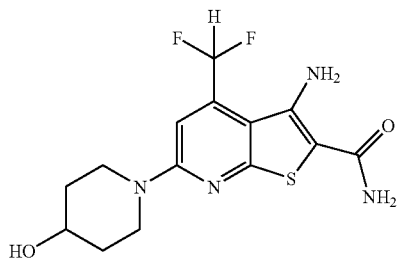

Prepared in analogous fashion to Example 2 using 4-hydroxypiperidine in place of 4-(N-methyl, N-Boc)aminopiperidine; calculated for $C_{14}H_{16}F_2N_4O_2S$ 342.36, see desired MH+ of 343.51 m/z.

3-Amino-4-(1-fluoro-1-methyl-ethyl)-6-(4-methanesulfonyl-piperidin-1-yl)-thieno[2,3-b]pyridine-2-carboxylic acid amide

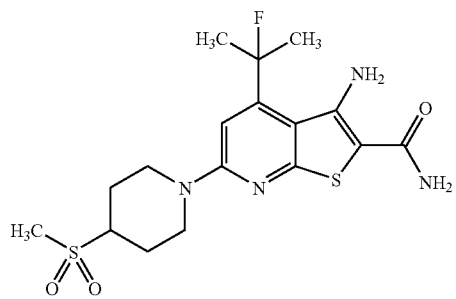

Prepared in analogous fashion to Example 1 using 2,6-dichloro-4-(1-fluoro-1-methyl-ethyl)-nicotinonitrile in place of 2,6-dichloro-4-(1,1-difluoro-propyl)-nicotinonitrile; calculated for $C_{17}H_{23}FN_4O_3S_2$ 414.50, see desired MH+ of 415.40 m/z.

Example D

Assessment of Biological Properties

The inhibition of IKKα and IKKβ by the compounds of the present invention can be determined with the following assay that measures the phosphorylation of the IκBα substrate by the respective kinases. The enzymes used in the assay were N-terminally flag-tagged versions of the human IKKβ or IKKα and the substrate was a GST fusion protein with IκBα (amino acids 1-54).

The reaction mixtures (60 μl) contained 20 mM HEPES pH 7.5, 10 mM $MgCl_2$, 2 mM $MnCl_2$, 100 mM NaCl, 100 μM $Na_3VO_4$, 20 mM β-glycerophosphate, 1 mM DTT, 2% DMSO, 250 nM ATP, 0.4 nM [$^{33}$P]ATP (specific activity, 3000 Ci/mmol), IκBα substrate, IKK enzyme and test compound. The reaction mixtures contained either 3.6 µg/ml IKKα and 245 µg/ml IκBα or 0.9 µg/ml IKKβ and 53 µg/ml IκBα.

Reactions were initiated by adding a solution of IκBα substrate and ATP to polypropylene plates containing IKK enzyme that was pre-incubated for 5 minutes with test compound. Then the reaction mixtures were incubated for 1 hour at 25° C., placed on ice and quenched by the addition of 150 µl 10% trichloroacetic acid and 5% disodium pyrophosphate. After mixing, the entire contents of the quenched reaction mixtures were transferred to a pre-wetted Packard UniFilter filtration plate, aspirated and washed 6 times with 250 µl of ddH$_2$O using the Packard Filtermate Harvester. Filtration plates were then air dried, supplemented with 40 µl of Microscint 20 scintillation fluid and the $^{33}$P-labeled reaction products were quantified using the Packard TopCount scintillation counter.

Compounds were tested in three-fold serial dilutions and inhibitor concentrations to achieve 50% inhibition of enzyme activity (i.e., IC$_{50}$) were derived from dose-response curves using SAS software (SAS Institute, Cary N.C.). A non-linear regression analysis based on the Hill equation was applied to the percent inhibition versus concentration data. In all cases, compound concentrations were verified by HPLC.

Compounds in the Tables in the Detailed Description of the Invention section were all evaluated in the assay for IKKβ inhibition and all had IC$_{50}$'s below 1 µM in this assay:

Example E

Enzyme Linked Immunosorbent Assay (ELISA)

ICAM-1 Expression on HeLa Cells

HeLa cells are seeded on 96 well tissue culture treated plates (Costar) in complete medium comprised of 10% decomplemented fetal bovine serum in RPMI1640 with gentamycin and L-glutamine and grown overnight to confluence. The following day, the media is changed and the wells are treated with test compounds. 10 mM DMSO stock solutions of compounds are serially diluted with 0.1% DMSO (final concentration)-screening media to 5 final concentrations (starting at 10 µM). Compounds are pre-incubated with cells for 30 min followed by stimulation with TNFα (R&D Systems) for 5-6 hr. The adherent cells are then assayed for expression of intercellular adhesion molecule-1 (ICAM-1). Monolayers are washed three times with D-PBS (Gibco) and fixed for 10 min at room temperature with 1% paraformaldehyde (Polysciences, Inc) diluted in D-PBS. After washing to remove fixative, the monolayers are blocked with 2% BSA-D-PBS overnight at 4° C. 100 µL of anti-ICAM-1 mAB RR1-HRP (diluted 1:5000 in 2% BSA-DPBS; Zymed custom conjugate of BIPI mAB) is added for 1 hr at 37° C. Wells are washed three times with D-PBS. 100 µL of ABTS substrate diluted in substrate buffer (Zymed) is added to each well. Optical absorbance is measured at 405 nm in a Thermomax microplate reader (Molecular Dynamics). Data is plotted as percent of control and IC$_{50}$s are determined using xlfit 4 model # 201.

Example F

Rat CIA Protocol

Effects of Compounds in 7 Day Rat Established Type II Collagen Arthritis

Purpose: To determine the dose responsive efficacy of compounds administered by oral gavage dosing bid in inhibiting the inflammation, cartilage destruction and bone resorption of established type II collagen arthritis in rats. The terminal pharmacokinetic component is included.

Animals: 36 (Order 42) Female Lewis rats (Harlan, 1173000), weighing 125-150 g on arrival. Extras are used because animals with arthritis are selected and there is not 100% incidence of disease in this model in the short time frame for enrollment (inject 42 with collagen to get 38 solid responders on days 10, 11 for 4 groups of 8. Four rats are used to serve as normal controls.

Materials: Agents or drugs in vehicle (Cremaphor), Type II collagen, Freund's incomplete adjuvant.

General Study Design: Animals (8/group for arthritis, 4/group for normal control), housed 4/cage, are acclimated for 4-8 days.

Acclimated animals are anesthetized with Isoflurane and given collagen injections (day 0). On day 6 they are anesthetized again for the second collagen injection. Collagen is prepared by making a 4 mg/ml solution in 0.01N Acetic acid. Equal volumes of collagen and Freund's incomplete adjuvant, are emulsified by hand mixing until a bead of this material holds its form when placed in water. Each animal receives 300 µl of the mixture each time spread over 3 subcutaneous sites on its back.

Calipering of normal (pre-disease) right and left ankle joints are done on day 9. On days 10-11, onset of arthritis occurs and rats are randomized into treatment groups. Randomization into each group is done after ankle joint swelling is obviously established in at least one hind paw.

After an animal is selected for enrollment in the study, treatment is initiated by the oral route. Animals given vehicle or compound doses are enrolled and BID dosing (12 hr intervals) initiated using a volume of 5 ml/kg for oral solutions. Rats are weighed on days 1-7 of arthritis and caliper measurements of ankles taken every day. Final body weights are taken on day 7 of arthritis. On day 7, animals are euthanized, both hind paws and knees are removed, hind paws are weighed and then (with knees) placed in formalin and then processed for microscopy.

PK Sampling Final (Day 6 of Arthritis)

On day 6 of arthritis, a pharmacokinetic analysis is done on groups 2-5 as follows using 8 rats/group: All animals are sampled to insure no stress bias in the data Animals 1, 2, 3, 4, 5, 6, 7, 8 draw samples at pre-dose (trough) on day 6. Then dose and pull samples are taken at 2, 4 and 8 hr.

Sampling occurs over 1-2 days depending on enrollment patterns and involves groups 2-7 for sample retention as all arthritic animals are bled similarly.

Blood samples: pull 0.35 ml of tail vein blood into syringes containing 0.03 ml of Heparin (100 IU/ml of saline, 1:9 ratio) at above times. Blood samples on kept ice until centrifugation to plasma.

Processing of Joints

The ankle joins are processed for 1-2 days in fixative and 4-5 days in decalcifier, and then cut in half longitudinally. Knees are cut in half in the frontal plane, processed, embedded, sectioned and stained with toluidine blue.

Scoring of Joints Collagen arthritic ankles and knees are given scores of 0-5 for inflammation, pannus formation and bone resorption according to the following criteria:

Knee and Ankle Inflammation

0=Normal

1=Minimal infiltration of inflammatory cells in particular tissue

2=Mild infiltration

3=Moderate infiltration with moderate edema

4=Marked infiltration with marked edema

5=Severe infiltration with severe edema

Ankle Pannus (Emphasis on Tibiotarsal Joint)

0=Normal

1=Minimal infiltration of pannus in cartilage and subchondral bone

2=Mild infiltration (<¼ of tibia at edges)

3=Moderate infiltration (¼ to ⅓ of tibia affected, smaller tarsals affected)

4=Marked infiltration (½-¾ of tibia affected, destruction of smaller tarsals)

5=Severe infiltration (>¾ of tibia affected, severe distortion of overall architecture)

Knee Pannus

0=Normal

1=Minimal infiltration of pannus in cartilage and subchondral bone

2=Mild infiltration (extends over up to ¼ of surface or subchondral area of tibia or femur)

3=Moderate infiltration (extends over >¼ but <½ of surface or subchondral area of tibia or femur)

4=Marked infiltration (extends over ½ to ¾ of tibial or femoral surface)

5=Severe infiltration (covers >¾ of surface)

Cartilage Damage (Ankle)

0=Normal

1=Minimal=minimal to mild loss of toluidine blue staining with no obvious chondrocyte loss or collagen disruption 2=Mild=mild loss of toluidine blue staining with focal mild (superficial) chondrocyte loss and/or collagen disruption and full destruction of tibia <¼ of surface, mild changes in smaller tarsals 3=Moderate=moderate loss of toluidine blue staining with multifocal moderate (depth to middle zone) chondrocyte loss and/or collagen disruption, ¼ to ⅓ of tibia affected by full thickness destruction, smaller tarsals affected to ½-¾ depth 4=Marked=marked loss of toluidine blue staining with multifocal marked (depth to deep zone) chondrocyte loss and/or collagen disruption, ½-¾ of tibia with full thickness destruction, destruction of smaller tarsals 5=Severe=severe diffuse loss of toluidine blue staining with multifocal severe (depth to tide mark) chondrocyte loss and/or collagen disruption Cartilage Damage (Knee, Emphasis on Femoral Condyles)

0=Normal

1=Minimal=minimal to mild loss of toluidine blue staining with no obvious chondrocyte loss or collagen disruption 2=Mild=mild loss of toluidine blue staining with focal mild (superficial) chondrocyte loss and/or collagen disruption 3=Moderate=moderate loss of toluidine blue staining with multifocal to diffuse moderate (depth to middle zone) chondrocyte loss and/or collagen disruption 4=Marked=marked loss of toluidine blue staining with multifocal to diffuse marked (depth to deep zone) chondrocyte loss and/or collagen disruption, 5=Severe=severe diffuse loss of toluidine blue staining with multifocal severe (depth to tide mark) chondrocyte loss and/or collagen disruption on both femur and tibia Bone Resorption (Ankle)

0=Normal

1=Minimal=small areas of resorption, not readily apparent on low magnification, rare osteoclasts 2=Mild=more numerous areas of resorption, not readily apparent on low magnification, osteoclasts more numerous, <¼ of tibia at edges is resorbed 3=Moderate=obvious resorption of medullary trabecular and cortical bone without full thickness defects in cortex, loss of some medullary trabeculae, lesion apparent on low magnification, osteoclasts more numerous, ¼ to ⅓ of tibia affected, smaller tarsals affected 4=Marked=Full thickness defects in cortical bone, often with distortion of profile of remaining cortical surface, marked loss of medullary bone, numerous osteoclasts, ½-¾ of tibia affected, destruction of smaller tarsals 5=Severe=Full thickness defects in cortical bone, often with distortion of profile of remaining cortical surface, marked loss of medullary bone, numerous osteoclasts, >¾ of tibia affected, severe distortion of overall architecture Bone Resorption (Knee)

0=Normal

1=Minimal=small areas of resorption, not readily apparent on low magnification, rare osteoclasts 2=Mild=more numerous areas of resorption, definite loss of subchondral bone involving ¼ of tibial or femoral surface (medial or lateral)

3=Moderate=obvious resorption of subchondral bone involving >¼ but <½ of tibial or femoral surface (medial or lateral)

4=Marked=obvious resorption of subchondral bone involving ≧½ but <¾ of tibial or femoral surface (medial or lateral)

5=Severe=distortion of entire joint due to destruction involving >¾ of tibial or femoral surface (medial or lateral)

Statistical Analysis.

Statistical analysis of body/paw weights and paw AUC and histopathology parameters are evaluated using a one-way analysis of variance (ANOVA). Individual group comparisons are made using the appropriate multiple comparison post-test. All tests have significance set at the 5% significance level.

Percent inhibition of paw weight and AUC is calculated using the following formula:

% Inhibition=A−B/A×100

A=Mean Disease Control−Mean Normal

B=Mean Treated−Mean Normal

We claim:

1. A compound of formula (I):

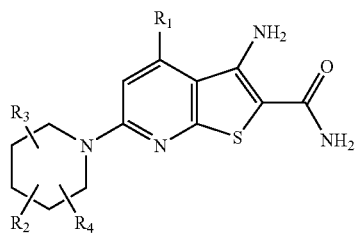

wherein:
$R_1$ is a partially halogenated $C_{1-6}$alkyl optionally substituted with one to two $R_5$;
$R_2$, $R_3$ and $R_4$ are independently selected from H, —S(O)$_n$ $C_{1-6}$alkyl, NR$_6$R$_7$, OH, CF$_3$ and $C_{1-6}$ alkyl;
$R_5$ is OH, CO$_2$H or $C_{1-6}$ alkoxy;
$R_6$ and $R_7$ are independently selected from H and $C_{1-6}$alkyl; and
n is 0, 1 or 2;
or a pharmaceutically acceptable salt thereof.

2. The compound according to claim 1 wherein:
$R_1$ is —CF$_2$H, —CF$_2$CH$_3$, —CF$_2$CH$_2$CH$_3$, —CF$_2$CH$_2$CH$_2$CH$_3$ or 1-fluoro-1-methyl ethyl;
$R_2$, $R_3$ and $R_4$ are independently selected from H, —S(O)$_n$ $C_{1-6}$alkyl, NR$_6$R$_7$, OH, CF$_3$ and $C_{1-6}$ alkyl;
$R_6$ and $R_7$ are independently selected from H and $C_{1-6}$alkyl.

3. The compound according to claim 1 wherein:
$R_1$ is —CF$_2$H, —CF$_2$CH$_2$CH$_3$ or 1-fluoro-1-methyl ethyl;
$R_2$ and $R_3$ and $R_4$ are selected from H, and —S(O)$_n$C$_{1-6}$ alkyl; and
$R_6$, $R_7$ are independently selected from H and $C_{1-6}$alkyl;
n is 0, 1 or 2.

4. A compound selected from the group consisting of:
3-Amino-6-(4-amino-piperidin-1-yl)-4-(1,1-difluoro-propyl)-thieno[2,3-b]pyridine-2-carboxylic acid amide;
3-Amino-6-((S)-4-amino-3,3-dimethyl-piperidin-1-yl)-4-(1,1-difluoro-propyl)-thieno[2,3-b]pyridine-2-carboxylic acid amide;
3-Amino-4-(1,1-difluoro-propyl)-6-(4-hydroxy-4-trifluoromethyl-piperidin-1-yl)-thieno[2,3-b]pyridine-2-carboxylic acid amide;
3-Amino-4-(1,1-difluoro-propyl)-6-(4-hydroxy-piperidin-1-yl)-thieno[2,3-b]pyridine-2-carboxylic acid amide;
3-Amino-6-(4-amino-4-methyl-piperidin-1-yl)-4-(1,1-difluoro-propyl)-thieno[2,3-b]pyridine-2-carboxylic acid amide;
3-Amino-4-(1,1-difluoro-propyl)-6-(4-methanesulfonyl-piperidin-1-yl)-thieno[2,3-b]pyridine-2-carboxylic acid amide;
3-Amino-6-(4-amino-piperidin-1-yl)-4-difluoromethyl-thieno[2,3-b]pyridine-2-carboxylic acid amide;
3-Amino-4-difluoromethyl-6-(4-hydroxy-piperidin-1-yl)-thieno[2,3-b]pyridine-2-carboxylic acid amide;
3-Amino-4-(1-fluoro-1-methyl-ethyl)-6-(4-methanesulfonyl-piperidin-1-yl)-thieno[2,3-b]pyridine-2-carboxylic acid amide;
3-Amino-4-(1,1-difluoro-propyl)-6-(4-hydroxy-4-methyl-piperidin-1-yl)-thieno[2,3-b]pyridine-2-carboxylic acid amide;
3-Amino-4-(1,1-difluoro-propyl)-6-(4-hydroxy-3,3-dimethyl-piperidin-1-yl)-thieno[2,3-b]pyridine-2-carboxylic acid amide;
3-Amino-4-difluoromethyl-6-(4-methylamino-piperidin-1-yl)-thieno[2,3-b]pyridine-2-carboxylic acid amide; and or a pharmaceutically acceptable salt thereof.

5. A pharmaceutical composition comprising a pharmaceutically effective amount of a compound according to claim 1.

* * * * *